(12) United States Patent
Lee et al.

(10) Patent No.: US 11,383,093 B1
(45) Date of Patent: Jul. 12, 2022

(54) RADIATION RELEASE CAPSULE

(71) Applicants: Hoseon Lee, Marietta, GA (US); Garrett S. Kolls, Alpharetta, GA (US)

(72) Inventors: Hoseon Lee, Marietta, GA (US); Garrett S. Kolls, Alpharetta, GA (US)

( * ) Notice: Subject to any disclaimer, the term of this patent is extended or adjusted under 35 U.S.C. 154(b) by 47 days.

(21) Appl. No.: 17/111,696

(22) Filed: Dec. 4, 2020

Related U.S. Application Data

(60) Provisional application No. 62/944,972, filed on Dec. 6, 2019.

(51) Int. Cl.
*A61N 5/10* (2006.01)
*A61N 2/00* (2006.01)
*A61N 1/40* (2006.01)
*A61N 2/02* (2006.01)

(52) U.S. Cl.
CPC ............ *A61N 2/002* (2013.01); *A61N 1/40* (2013.01); *A61N 2/02* (2013.01); *A61N 5/1007* (2013.01); *A61N 2005/1011* (2013.01)

(58) Field of Classification Search
CPC .... A61N 2005/1019; A61N 2005/1024; A61N 5/1005; A61N 5/1014; A61N 5/1015
See application file for complete search history.

(56) References Cited

U.S. PATENT DOCUMENTS

| | | | |
|---|---|---|---|
| 5,213,561 A * | 5/1993 | Weinstein | A61N 5/1002 600/7 |
| 5,713,828 A | 2/1998 | Coniglione | |
| 6,196,963 B1 | 3/2001 | Williams | |
| 6,413,204 B1 | 7/2002 | Winkler et al. | |
| 6,450,938 B1 | 9/2002 | Miller | |
| 6,632,176 B2 | 10/2003 | McIntire et al. | |
| 6,746,661 B2 | 6/2004 | Kaplan | |
| 7,736,293 B2 | 6/2010 | Lamoureux et al. | |
| 7,831,308 B2 | 11/2010 | Rezai et al. | |
| 8,114,007 B2 | 2/2012 | Lamoureux et al. | |
| 8,517,906 B2 | 8/2013 | Lubock | |
| 8,562,504 B2 | 10/2013 | White et al. | |
| 2001/0037083 A1 | 11/2001 | Hartlaub et al. | |
| 2004/0082908 A1 | 4/2004 | Whitehurst et al. | |
| 2006/0235260 A1 * | 10/2006 | Mourtada | A61N 5/1016 600/7 |

(Continued)

*Primary Examiner* — Samuel G Gilbert
(74) *Attorney, Agent, or Firm* — H. Brock Kolls

(57) ABSTRACT

The present invention relates to a radiation release capsule for controlling radiation exposure and selectively providing electromagnetic pulse therapy, electric field therapy, or treatment drug or gas delivery at a treatment site associated with a treatment environment in accordance with a treatment cycle. The radiation release capsule includes an inner housing that is radiopaque, the inner housing includes an aperture and defines a cavity configured to at least encompass a radiation source. An outer housing is radiopaque. A case is radiation permeable and surrounds the inner housing and outer housing. One of the housing is repositionable blocking all or some of the aperture through which radiation dosage is directionally delivered to the treatment site. A control system operates the radiation release capsule. The capsule can be operated locally by an authorized person to deliver treatment or wirelessly data communicate and be managed remotely in telemedicine applications.

20 Claims, 10 Drawing Sheets

(56) References Cited

U.S. PATENT DOCUMENTS

2011/0270395 A1* 11/2011 Blackwell ............. A61F 2/4465
　　　　　　　　　　　　　　　　　　　　　　　　　　600/3
2013/0102832 A1　　4/2013　Hoedl et al.
2017/0100539 A1　　4/2017　Hood et al.

* cited by examiner

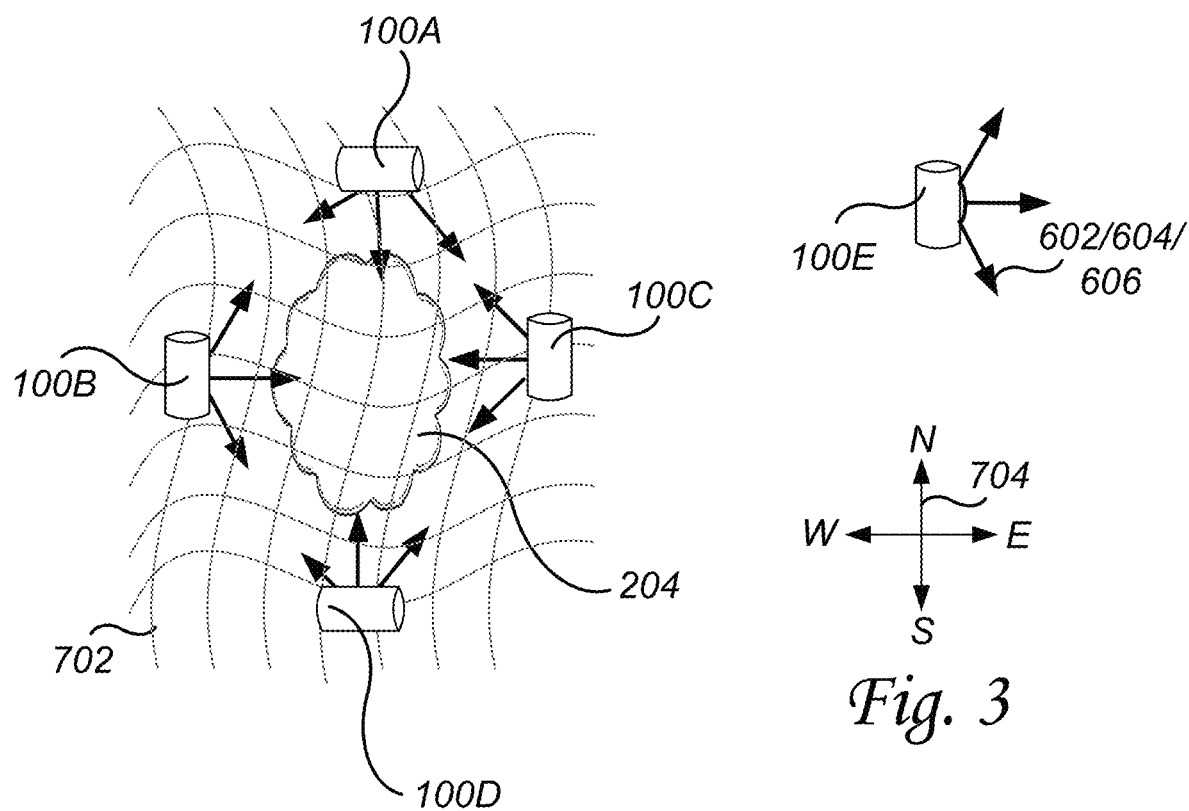
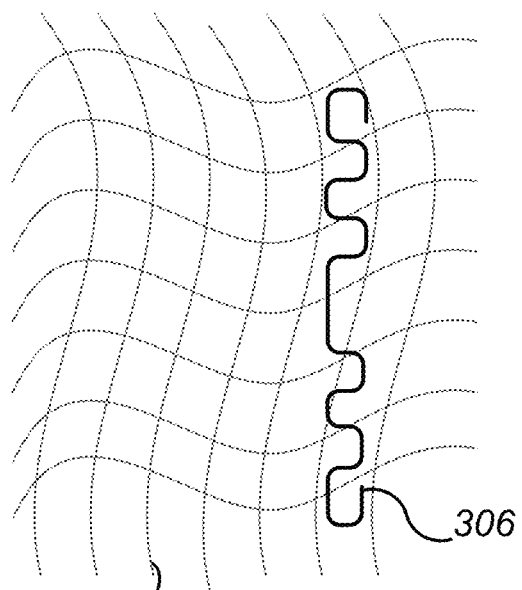
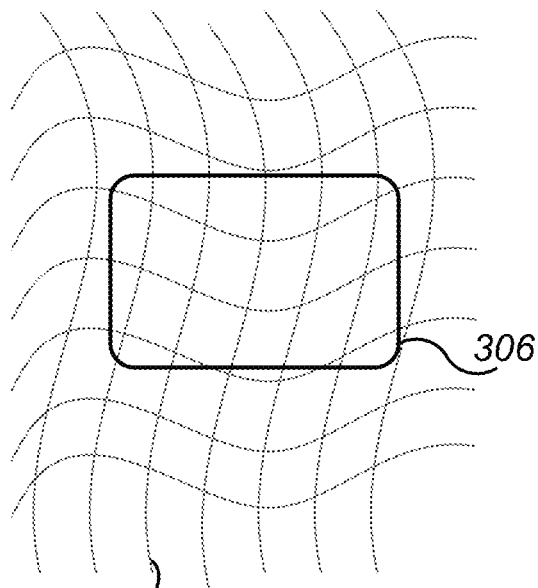

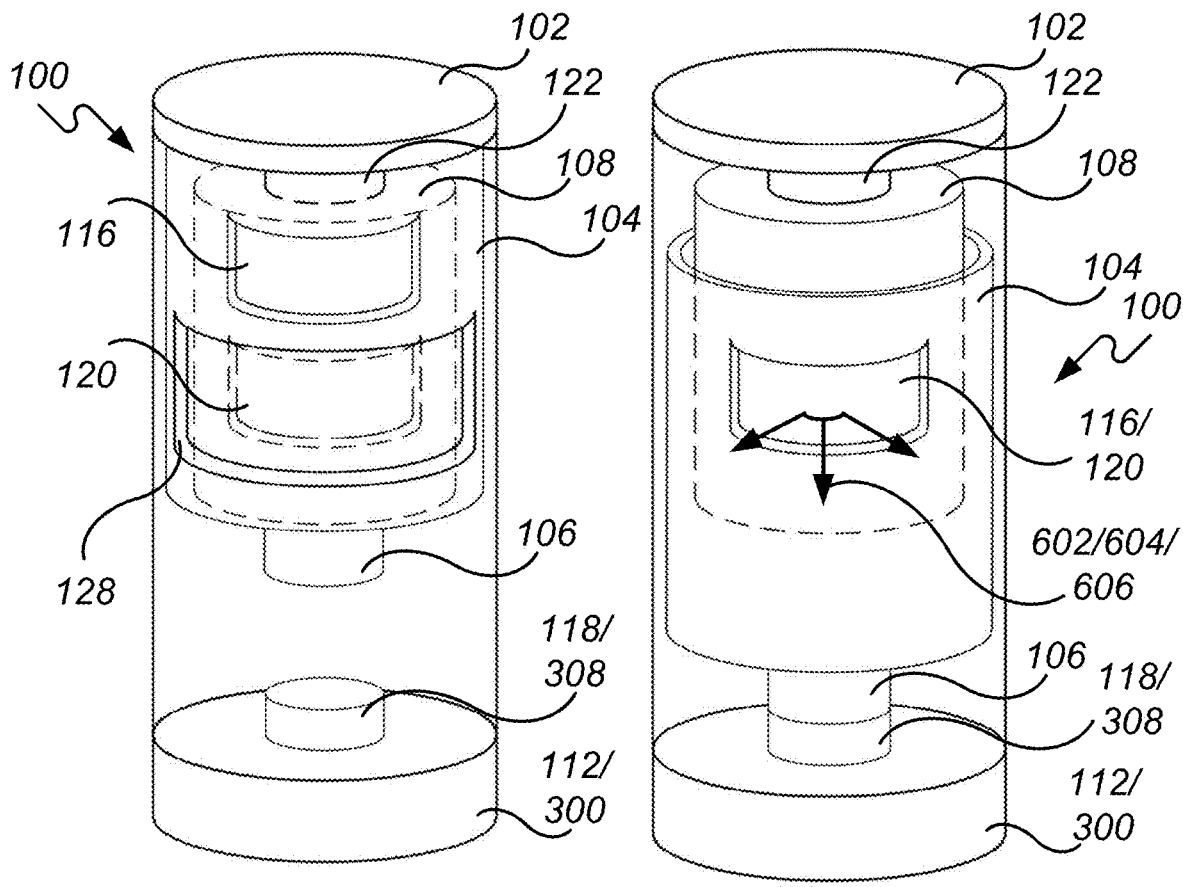
*Fig. 6A*  *Fig. 6B*
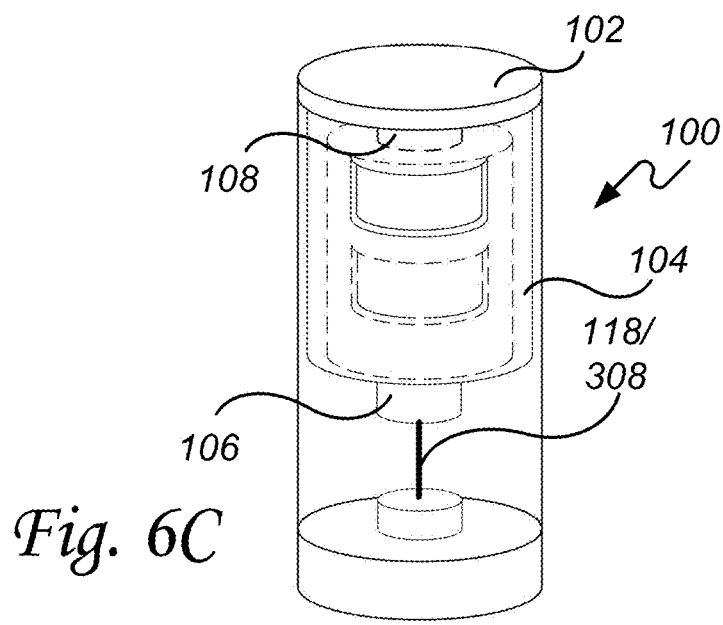
*Fig. 6C*

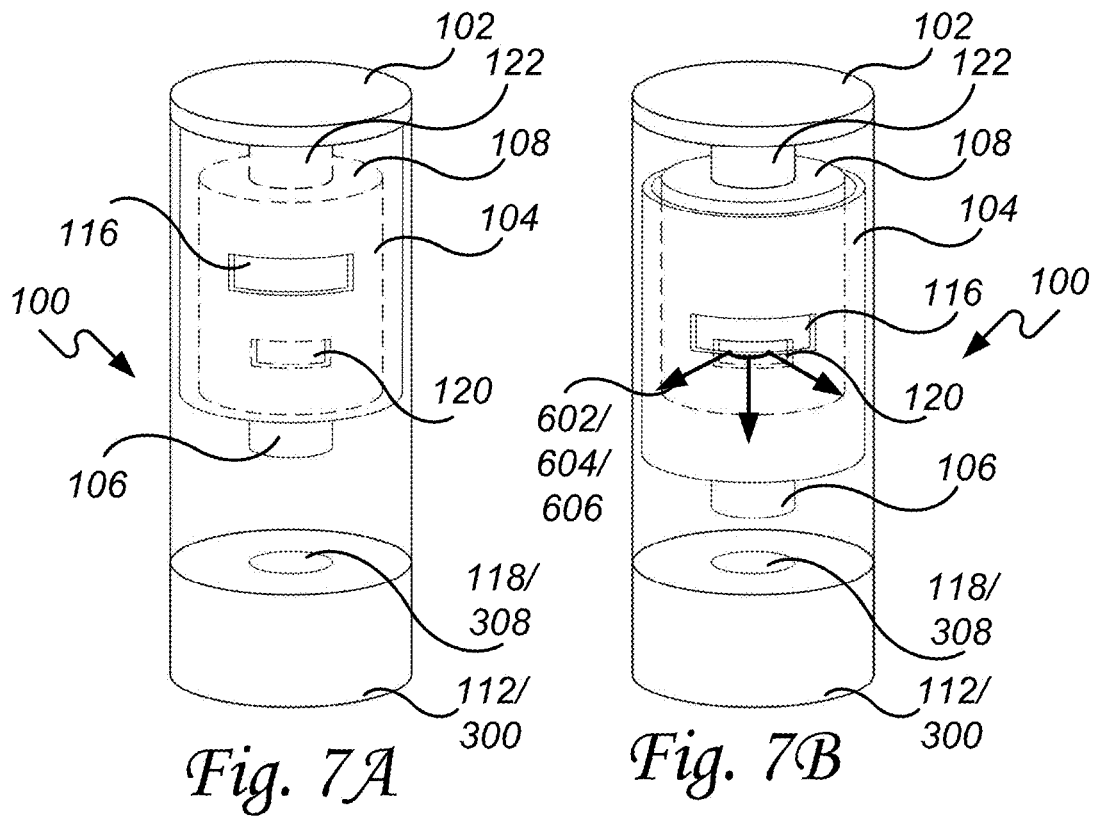
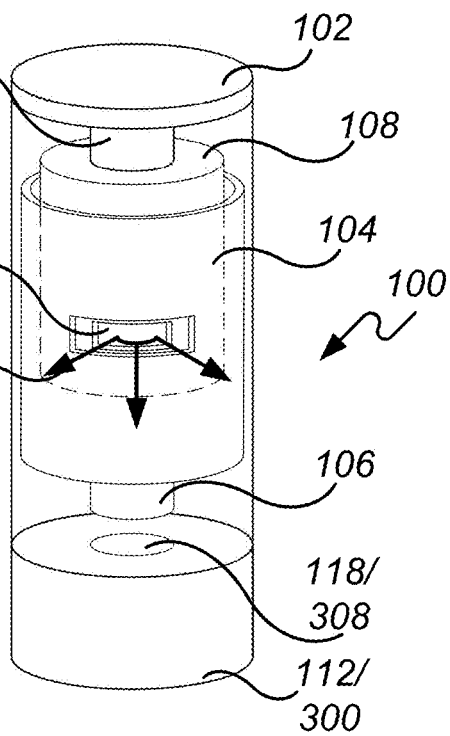
Fig. 7A  Fig. 7B  Fig. 7C

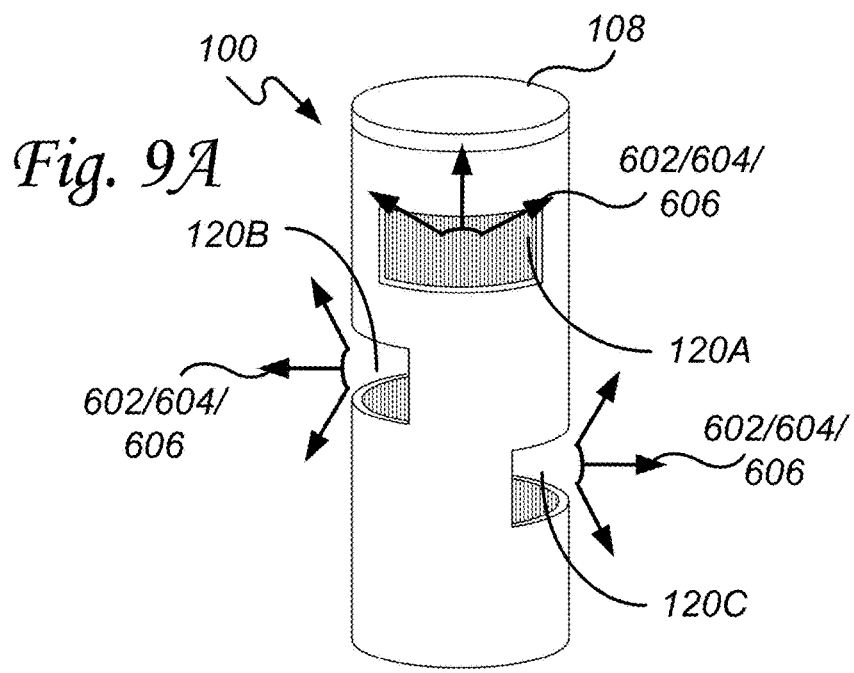
Fig. 9A
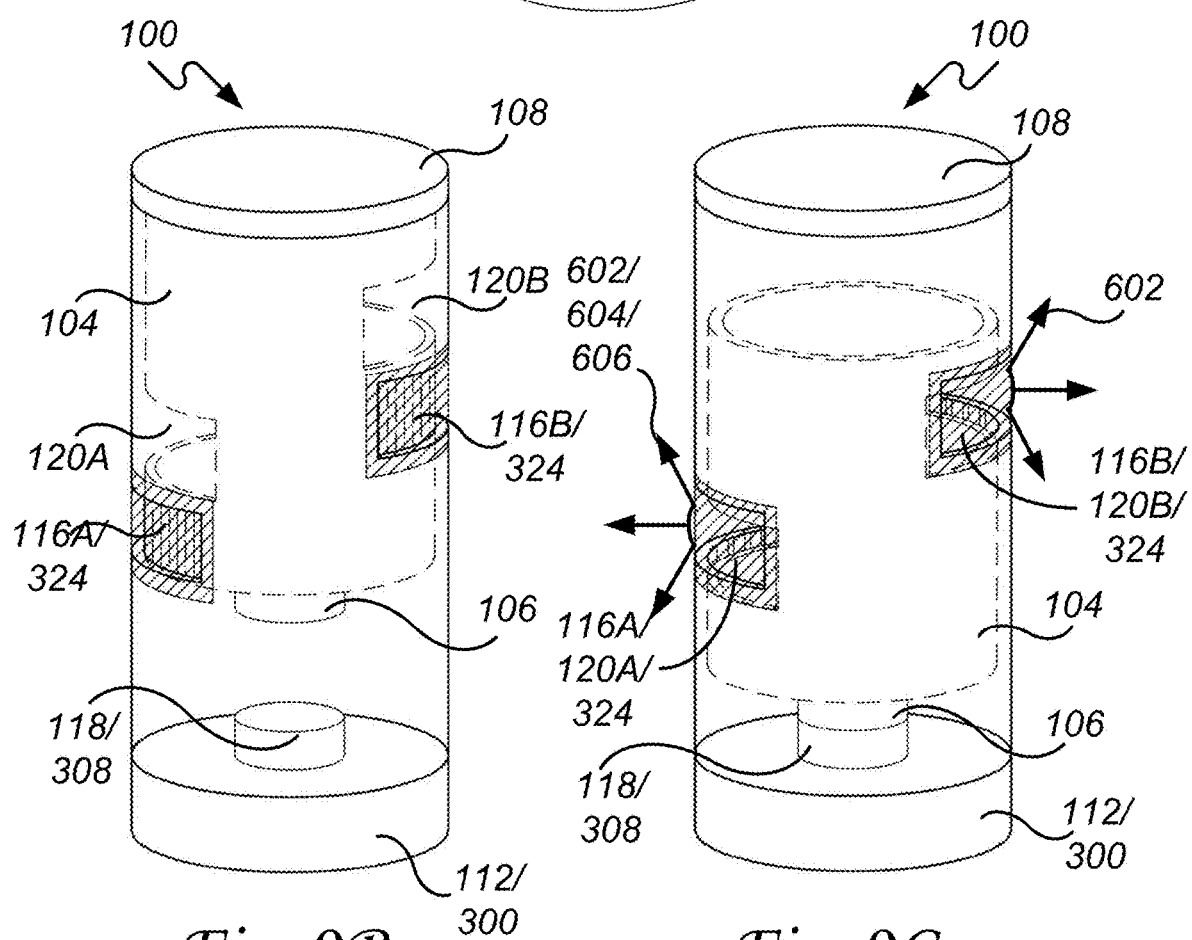
Fig. 9B
Fig. 9C

RADIATION RELEASE CAPSULE

CROSS-REFERENCE TO RELATED APPLICATIONS

This application contains subject matter which is related to the subject matter of the following application. The below listed application is hereby incorporated herein by reference in its entirety:

This is a U.S. non-provisional application that claims the benefit of a U.S. provisional application, Ser. No. 62/944,972, inventor Hoseon Lee, entitled "IMPLANTABLE RADIATION SOURCE", filed Dec. 6, 2019.

TECHNICAL FIELD OF THE INVENTION

This invention relates to a radiation release capsule for controlling radiation exposure and selectively providing electromagnetic pulse therapy, electric field therapy, or treatment drug or gas delivery at a treatment site associated with a treatment environment in accordance with a treatment cycle.

BACKGROUND OF THE INVENTION

Before our invention, the disadvantages and shortcomings for current radiation pellets or sources placed in the body is that the radiation directionality and exposure amount cannot be controlled. In this regard, the radiation cannot be turned on or off, the dosage amount cannot be controlled remotely, and directivity of the radiation cannot be controlled once the radiation source is implanted. In cases when radiation pellets drift or move away from the tumor towards healthy tissues and critical organs, there is no ability to turn off the radiation for implanted sources, without undergoing surgery. Due to these restrictions, there have been only two treatment methods for brachytherapy, low dose rate (LDR) brachytherapy which can only use low energy for a longer period of treatment time to treat tumors with radiation seeds within the body, or high dose rate (HDR) brachytherapy, which uses several doses of high energy radiation, which requires hospital visits for each dose, and has a higher chance of risk to healthy cells and tissue. There is currently no method of controlling the dose rate to any level between LDR and HDR with directional radiation beams from within the body, that minimizes risk compared to external beam radiation and is more cost effective than proton therapy.

For uterine, cervical, esophageal, lung, and head and neck cancer, tubes have to be placed through the cavity to the target area often in multiple treatments on separate days for each fraction of treatment. The repeatability issues and tedious setup issues are a current challenge for providing accurate dosing and cause inconvenience for the patient. Furthermore, blocking radiation towards healthy organs and tissues while the radiation source is applied is an issue. Currently for high dose rate (HDR), a catheter on a long tube with a small isotropic radiation source attached to the end is placed in the target area for a short period of time. However, this radiation is isotropic, and for certain cancers, such as the uterine, cervical, esophageal, lung, and head and neck cancers, it is difficult to control directivity of the radiation and difficult to control repeatability of location for consecutive sessions. The invention can be implanted after surgical resection at the site of most likely recurrence and subsequently removed following completion of treatment. HDR brachytherapy is also used for treatment of recurrent cancers where candidates are not candidates for surgical resection or re-treatment with external beam radiation due to the dose tolerance of adjacent normal tissue. The invention can be used to more precisely deliver high dose to the tumor while minimizing dose to normal structures compared to convention HRD delivery approaches.

Additional shortcomings of current technologies include the inability to control localized radiation treatment both inside and outside of the clinic or hospital where radiation treatment is administered. Furthermore, there is no method of remotely measuring doses of radiation within the body or the direction or radiation emission in real-time, from outside the body. Radiation detectors include photodiodes, phototransistors, photovoltaic sensors, and charge coupled devices (CCD), and Chrenkov luminescence imaging (CLI), among others. However, there has been no method of utilizing these radiation detectors inside the body, where the radiation dose is measured in real-time remotely from outside the body. In this regard, remotely monitoring, adjusting radiation dosage, directionality of exposure, even stopping radiation exposure cannot be effectuated with conventional treatment technologies. As such, often additional hospital visits and surgeries are required to manage control of the dosage over extended periods of time, depending on the prescribed radiation treatment.

Conventional product and process may include radiation pellets. The current products are radiation seeds, pellets, balloons, or sources of various sizes and shapes, as well as meshes and sheets containing arrays of radiation sources, depending on the cancer type and cancer treatment. As an example, a catheter, probe, tube, port, or other is used to insert or place the radiation sources in the targeted area. Surgery is done to open the target area to place radiation sources, sheets, meshes, or other, in the target area.

The present invention addresses this and other shortcomings by enabling the placement of radiation sources in target areas after surgery to destroy any residual tumor cells in a controlled manner. The directional radiation helps to minimize radiation to healthy cells, tissue, and nervous system, and the ability to control the dose rate can help reduce treatment time. The combination of directionality and dose control within the body enables customized treatment with minimal risk and maximum effectiveness. The radiation detectors integrated with the device can measure both the radiation direction and doses in real-time. Furthermore, hospital visits can be reduced by being able to control the radiation dosage remotely over a period of days, weeks, or months, depending on the prescribed radiation treatment. For these reasons and shortcomings as well as other reasons and shortcomings there is a long felt need that gives rise to the present invention.

SUMMARY OF THE INVENTION

The shortcomings of the prior art are overcome and additional advantages are provided through the provision of a radiation release capsule for controlling radiation exposure and selectively providing electromagnetic pulse therapy, electric field therapy, or treatment drug or gas delivery at a treatment site associated with a treatment environment in accordance with a treatment cycle.

The radiation release capsule comprising an inner housing that is radiopaque, the inner housing defines a cavity configured to at least encompass a radiation source. The inner housing having one or more of an aperture disposed through the inner housing to allow radiation from the radiation source to be directionally released during the treatment cycle. An outer housing is radiopaque and positioned proximate the inner housing. A case is radiation permeable and surrounds the inner housing and outer housing. Either the inner housing is stationary and the outer housing is slidable relative to the inner housing or the outer housing is stationary and the inner housing is slidable relative to the outer housing to control directionality and dosage of the radiation delivered to the treatment site by unblocking, blocking, or partially blocking the aperture.

Additional shortcomings of the prior art are overcome and additional advantages are provided through the provision of a radiation release capsule for controlling radiation exposure and selectively providing electromagnetic pulse therapy, electric field therapy, or treatment drug or gas delivery at a treatment site associated with a treatment environment in accordance with a treatment cycle.

The radiation release capsule comprising an inner housing that is radiopaque, the inner housing defines a cavity configured to at least encompass a radiation source. The inner housing having one or more of an aperture disposed through the inner housing to allow radiation from the radiation source to be directionally released during the treatment cycle. An outer housing is radiopaque and positioned proximate the inner housing. A case is radiation permeable and surrounds the inner housing and outer housing. Either the inner housing is stationary and the outer housing is slidable relative to the inner housing or the outer housing is stationary and the inner housing is slidable relative to the outer housing to control directionality and dosage of radiation delivered to the treatment site by unblocking, blocking, or partially blocking the aperture. A controller comprising a microcontroller, a memory, a radiation detector, a wireless communication interface, and an activation control, is configured to slidably position either the inner housing or the outer housing, the memory is encoded with instructions that when executed by the microcontroller perform the following steps of: receiving the treatment cycle from a digital device, by way of a wireless communication interface, the controller comprises the wireless communication interface, the treatment cycle, by way of the controller, effectuates delivery of a desired radiation dosage amount for a prescribed treatment period to the treatment site by transitioning between: Exposing, by slidably repositioning the outer housing or the inner housing so that at least portion of the aperture is unblocked by the outer housing engendering radiation delivery to the treatment site. Reading the direction of radiation and radiation level by way of the radiation detector. Comparing the radiation level to the desired radiation dosage amount. Adjusting the radiation level to match the desired radiation dosage amount by slidably repositioning the outer housing or the inner housing to increase or decrease the radiation level accordingly, wherein returning to the step of reading until the prescribed treatment period is complete. And blocking the aperture, with the outer housing, preventing radiation delivery to the treatment site.

Additionally, shortcomings of the prior art are overcome and additional advantages are provided through the provision of a method of controlling radiation exposure and selectively providing electromagnetic pulse therapy, electric field therapy, or treatment drug or gas delivery at a treatment site associated with a treatment environment in accordance with a treatment cycle.

The method comprising the steps of: positioning one or more of a radiation release capsule at the treatment site. The radiation release capsule comprising a controller, an outer housing that is radiopaque, an inner housing that is radiopaque. The inner housing defines a cavity configured to at least encompass a radiation source. The inner housing having one or more of an aperture disposed through the inner housing to allow radiation from the radiation source to be directionally released during the treatment cycle. The outer housing is positioned proximate the inner housing. A case is radiation permeable and surrounds the inner housing and outer housing. Either the inner housing is stationary and the outer housing is slidable relative to the inner housing or the outer housing is stationary and the inner housing is slidable relative to the outer housing to control directionality and dosage of radiation delivered to the treatment site by unblocking, blocking, or partially blocking the aperture. In an exemplary embodiment, some of the sensing elements of the radiation detector 324 can cover the aperture 116 openings of outer housing 104 so that when the inner 120 and outer 116 housings are aligned the radiation detector detects the radiation being emitted in real-time.

The method continues by delivering the treatment cycle by way of the controller, the controller comprising a microcontroller, a memory, and an activation control, the activation control is configured to slidably reposition either the inner housing or the outer housing. The memory is encoded with instructions that when executed by the microcontroller perform the following steps of transitioning between: exposing, by slidably repositioning the outer housing or the inner housing so that at least portion of the aperture is unblocked by the outer housing engendering radiation delivery to the treatment site, and blocking the aperture, with the outer housing, preventing radiation delivery to the treatment site.

Systems, manufacturing, and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and to the drawings.

BRIEF DESCRIPTION OF THE FIGURES

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 3 illustrates one example of a biocompatible mesh comprising a plurality of radiation release capsules positioned and secured thereon;

FIGS. 4A and 4B illustrate examples of a biocompatible mesh comprising an antenna. The antenna is conductive and electrically insulated from the biocompatible mesh;

FIGS. 6A, 6B, and 6C illustrate one example of the radiation release capsule having an activation control and operating to turn "on" and "off" radiation exposure at a treatment site;

FIGS. 7A, 7B, and 7C illustrate one example of a radiation release capsule regulating the radiation exposure at a treatment site by controlling the aperture opening in the inner housing;

FIGS. 9A, 9B, and 9C illustrate one example of radiation, treatment drug, or treatment gas directivity control by having a plurality of apertures located on different sides and at different heights on the inner housing and outer housing;

Figure 1:
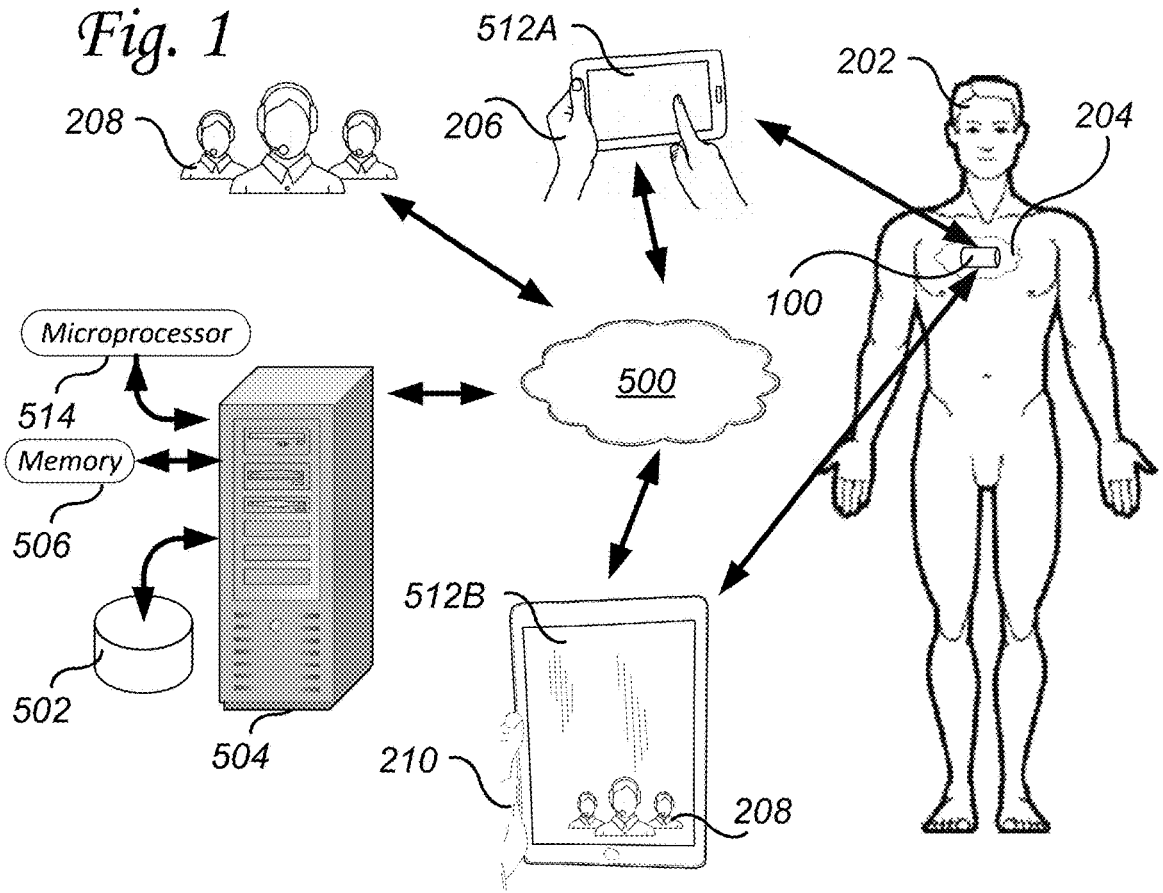
FIG. 1 illustrates one example of a system, network, and digital devices for remotely managing radiation release capsules.

The detailed description explains the preferred embodiments of the invention, together with advantages and features, by way of example with reference to the drawings.

DETAILED DESCRIPTION OF THE INVENTION

With reference to the Figures, an advantage in the present invention is the ability to turn "on", "off", and control the directivity and exposure amount of radiation, from a radiation source 602, after implantation in a treatment environment 202. Doing so improves repeatability and thus the effectiveness of the treatment. In addition, radiation exposure can be minimized towards healthy areas, maximized towards the target tumor area, also referred to as the treatment area 204, and turning "off" the radiation at the end of the treatment cycle and/or if the radiation source 602 pellet moves or drifts within the body, also referred to as the treatment environment 202, towards healthy tissue, critical organs, or away from the treatment site 204.

In contrast, shortcomings in the prior art are the inability to control the radiation exposure duration. In this regard, once implanted, the radiation source emanated constant radiation until the radiation energy is depleted or the radiation source is removed from the treatment environment. Advantages in the present invention allow for control of the radiation emission dosage and duration. In this regard, the radiation release capsule 100 encloses the radiation 602 and can effectively turn "off" or "on" radiation exposure to the treatment site 204, as well as vary control the directionality of the radiation beams emanating from the radiation release capsule 100, the dosage amount, and/or intensity of radiation delivered to the treatment site 204.

The systems, networks, radiation release capsule 100, and methods described herein comprise a plurality of exemplary embodiments and technical advantages, including, as examples and not a limitations: 1) The electrically controlled stop and release of radiation, from a radiation source 602, inside the body 202 also referred to as the treatment environment 202; 2) Radiation shielding material with any type of aperture that can be opened or closed to release or shield, stopping, radiation release; 3) Integration of the radiation shielding material, also referred to as inner housing 108 and outer housing 104, with a microcontroller 302 to program when and for how long the radiation 602 is released based on radiation dosage prescription; 4) Control the directivity of the radiation using apertures 116 and 120 and minimizing radiation directed towards healthy tissues/organs while maximizing radiation directed towards target areas referred to as a treatment site 204; 5) Turn off the radiation when and if the implanted radiation source completes a treatment cycle and/or drifts away from the targeted area 204 and towards healthy tissue and/organs; and 6) Improve repeatability in terms of the placement of the radiation source in the target treatment site 204 areas, which can help to improve the effectiveness and patient outcome.

Additional exemplary embodiments of the systems, radiation release capsule 100, and/or methods described herein comprise several technical advantages, including, as examples and not limitations: 1) A radiation release capsule 100 for controlling radiation 602 exposure and selectively delivering treatment drugs 604 or treatment gases 606 at a treatment site 204 associated with a treatment environment 202 in accordance with a treatment cycle; 2) A method of controlling radiation 602 exposure and selectively delivering treatment drugs 604 or treatment gases 606 at a treatment site 204 associated with a treatment environment 202 in accordance with a treatment cycle; 3) Providing telemedicine management and control of implanted radiation sources, and 4) Applications of biocompatible mesh 702 for securing one or more radiation release capsules 100 proximate the treatment site 204.

In the present invention the term "selectively" is intended to mean choosing between a list of choices included not making a selection at all. As an example, "The inner housing 108 or the outer housing 104 is repositionable, blocking all or some of inner housing 108 aperture 120 to control directionality and dosage of radiation exposure and, selectively the treatment drug delivery or the treatment gas delivery to the treatment site". In this example, none, one, or both of a treatment drug or a treatment gas can be delivered to the treatment site. As another example, "An outer housing is radiopaque, the outer housing, selectively having a one or more of aperture disposed through the outer housing. In this example, the outer housing might have none, one, or more than one of an aperture in the outer housing. In a third example, "A case comprising, selectively a plurality of apertures disposed through the case". In this example, the case might have none, one, or more of an aperture.

In an exemplary embodiment, treatment drug 604 can include, antibiotics, steroids, anti-retroviral drugs, pain relievers, hormones, chemotherapy drugs, drug therapy cocktails, and/or other types and kinds of treatment drugs, as may be required and/or desired in a particular embodiment. In an exemplary embodiment, treatment gas 606 can include oxygen, inert gases, and/or other types and kinds of treatment gases, as may be required and/or desired in a particular embodiment.

In an exemplary embodiment, a radiation release capsule comprises an inner housing 108 and an outer housing 104 that can be concentric, hollow cylindrical, square, rectangular, or other forms of shells with apertures disposed through the inner housing 108 and/or, selectively disposed through the outer housing 104. Such apertures can also be referred to as holes, windows, slots, or openings. In operation, when the inner housing 108 and outer housing 104 slides up, down, left, or right, to some degree relative to one another the apertures will either open, close, or partly open or close providing access to a cavity within the inner housing 108. The cavity comprising a radiation source 602 and, selectively treatment drugs 604 or treatment gas 606 that can be delivered at a treatment site 204. In short, access to the cavity by way of the apertures allows the radiation 602 emanating from the radiation source, seed, pellet, or selectively treatment drugs 604 or treatment gas 606 to emanate out of the radiation release capsule and into the treatment site 204 surrounding the radiation release capsule 100. In a plurality of other exemplary embodiments, the radiation source 602 can be of any radiation source, not limited to pellets.

In an exemplary embodiment, a microcontroller 302 is attached to activation control 308. The activation control 308 can be connected to an electromagnet 314 or a shape-memory polymer. The microcontroller 302 can be programmed to turn "on" and "off" the electromagnet 314 with different polarities so that the electromagnet 314 can move the inner housing 108 or outer housing 104 depending on radiation release capsule 100 configurations so that the aperture 116 and 120 openings in the inner housing 108 or outer housing 104 are either open providing access to the inner housing 108 cavity, closed preventing access to the inner housing 108 cavity, or partly open where the apertures 116 and 120 in the inner housing 108 and outer housing 104 slight overlap. While in an open or partly open state configuration the radiation 602, from the radiation source, is allowed to emanate directionally from the aperture 120 out of the radiation release capsule 100 while in the closed configuration the radiation 602 is blocked from leaving the radiation release capsule 100. The degree of partial opening of the apertures 116 and 120 overlap openings in the inner housing and outer housing can be adjusted to control the amount, degree, directionality, and dosage of the radiation to be allowed to emanate outside of the radiation release capsule 100 and into the treatment site 204.

Shortcomings of the prior art that are overcome and are advantages in exemplary embodiments of the present invention include the inability to remotely control the radiation sources for brachytherapy. In prior art devices, the directivity of the radiation beams cannot be controlled once the radiation source is in the body, and the radiation cannot be turned "on" and "off". Controlling radiation directivity is a key issue that has not been able to be solved easily. For breast cancer, there is a higher risk of exposure to the heart, lungs, and spleen due to brachytherapy, which can cause heart problems, damage to the organs and normal tissue, and even cause secondary cancer. Due to this risk, the radiation dose is limited for brachytherapy and the treatment is not as effective as it could be. There have been efforts to try and address this issue of radiation directivity, but prior art solutions can only provide static directivity in one direction and cannot be controlled. One commercial product, Civa Sheet, is a flexible sheet that has a 2D array of radiation seeds with one side coated with gold to block radiation. This allows for a static, one-directional beam from the 2D array Civa Sheet. However, this directivity is static, is still not controllable, and cannot be turned on and off, ultimately limiting the dose amount. The Civa Sheet does not have an antenna structure embedded in the sheets and also cannot relay information wirelessly outside of the body. In exemplary embodiments of the present invention, a radiation release capsule 100 can control the directivity in any direction, turn the radiation source "on" and "off", and modulate the radiation dose, remotely outside the treatment environment 202 as well as by way of remote telemedicine over a global communication network 500 such as the Internet.

Additional, shortcomings of the prior art that are overcome and an advantage in exemplary embodiments of the present invention include the repeatability of radiation dose delivery to the treatment site due to the difficulty of placing the radiation source exactly in the same location in the body, especially for tumors in areas that are difficult to see. This applies to certain tumor locations for breast cancer but also includes cervical and esophageal cancer, which is difficult to visually verify the location for dose delivery. The problem with prior art solutions that are overcome in the present invention is that there can be errors in position accuracy in the day-to-day tedious manual setup process to deliver the radiation dose to the same location each day. As a result, this can lower treatment efficacy and increase the risk to organs and normal tissue. The radiation release capsule 100 of the present invention can be implanted and fixed in the precise location for dose delivery, which minimizes the position error, minimizes the risk of exposure to non-tumor areas, and streamlines the setup process.

As a further example, military servicewomen have a 20-40% higher chance of breast cancer than those in the general population. Also, many women veterans live in rural areas, which have fewer numbers of radiation treatment centers. Not only military servicewomen and veteran women but also African American and Hispanic American women have disparities in access to radiotherapy, which is sadly consistent with the general trend for underrepresented minorities. There are significant barriers for Appalachian patients with cancer to receive radiotherapy, in part due to the number and quality of radiation centers that are accessible to this patient population. Research has shown that travel burden is an important factor affecting access to appropriate and current cancer diagnosis and treatment and that it can worsen the achievement of universal high-quality care for cancer patients. By controlling the opening and closing of the shielding, the radiation release capsule, system, and/or methods of the present invention can deliver multiple doses per day, including on weekends to shorten the total treatment period and significantly reduce the number of hospital visits.

Another shortcoming of the prior art that is overcome and an advantage in exemplary embodiments of the present invention are the drawbacks of traditional radiation therapy including daily trips to the hospital for treatments, typically five days a week for five to seven weeks or more. Also, it may expose healthy tissue, such as the heart and lungs, to radiation.

In an exemplary embodiment, the present invention makes use of the remotely controlled on-and-off operation using inner housing 108 and outer housing 104 positioning having apertures to manipulate an implantable radioactive source ranging from low dose rate (LDR) to high dose rate (HDR) brachytherapy for the treatment of breast cancer as well as other cancer types. For breast cancer, external beam radiotherapy (EBRT) is widely used and in some cases, HDR or LDR brachytherapy can be used to eliminate residual cancer cells in the periphery of the area where the tumor was removed. In some cases, the tumor may be too close in proximity to critical organs in the body, and the tumor cannot be cut out or removed physically, in which case brachytherapy is prescribed. However, a major challenge overcome by the present invention is minimizing radiation exposure to critical organs (e.g. heart, lungs) and healthy tissue, and maximizing the directivity towards the area of the tumor and residual cancer cells.

Treatments involving radiation are most commonly used as a means to kill cancer cells and shrink tumors. There are non-invasive radiation treatments such as external beam radiation. There are also invasive radiation treatments that use radiation pellets, tubes, seeds, and balloons of various sizes, energy levels, and radiation intensities.

A shortcoming of the prior art that is overcome and an advantage in exemplary embodiments of the present invention is in the area of brachytherapy applications. Brachytherapy falls into three categories a high-dose-rate, a low-dose-rate, and within that, a pulse-dose-rate. The high-dose-rate uses a powerful radioactive source that is inserted through an applicator, usually a catheter, for only a few minutes. Low-dose-rate brachytherapy uses a lower dose radiation source that is surgically implanted into the body for anywhere from a day to permanently. The permanent implants, usually called seeds or pellets, are the size of grains of rice and lose their radioactivity over time. Pulse-dose-rate combines some advantages of both, having the physical effect of high-dose-rate and the radiobiological effects of low-dose-rate. Some researchers have improved the low-dose-rate brachytherapy by directing the radiation from the seeds using one-sided shielding. The healthy tissue is then spared the full dose of radiation on the shielded side, while the tumor gets the full dose from the unshielded side. These methods have had positive results. However, a shortcoming of the prior art that is overcome and an advantage in exemplary embodiments of the present invention is that there is still no control over remotely turning "on" and "off" the shielding around the radiation source.

There is a range of radionuclides used in brachytherapy. They range from low dose sources such as Iodine-125 to higher dose sources such as Cobalt-60, each having different characteristics such as dose rates, energies, and half-lives. The types of shielding necessary depend on the isotope used. For low energy isotopes such as Iodine-125, only a thin shield, such as a thin sheet of lead is needed. However, higher energy isotopes such as Cobalt-60 require a thicker shielding material. To calculate the shielding thickness, the following formula is used:

$$x = \frac{\ln\left(\frac{I_o}{I_x}\right)}{\mu}$$

Where x, $I_o$, $I_x$, p are the shielding thickness, dose rate at the source, desired dose rate, and the attenuation of the coefficient of the shielding material at the energy level of the source, respectively.

Iodine-125 makes a good source due to its relatively low energy of around 29 keV and is commonly used in current brachytherapy treatment. The maximum received dose from both internal and external radiation for the public is 100 milligram/year, or 1 mSv/year, which is equivalent to 0.114 µSv/hr. Therefore, assuming 250 mSv/hr dose rate at the source, desired dose rate of 0.114 µS/hr, and attenuation coefficient of 531.69 for gold at 30 keV, the shielding thickness would be less than 0.274 mm.

A shortcoming of the prior art that is overcome and an advantage in exemplary embodiments of the present invention relates to an implantable radiation source with controlled radiation directivity and dose modulation. Such a controllable radiation source exposure can help to minimize risk to normal tissue and/organs and improve overall dose treatment efficacy as well as efficiency over conventional brachytherapy.

In an exemplary embodiment, an inner housing 108 that is radiopaque defines a cavity configured to at least encompass a radiation source 602 and, optionally, a treatment drug 604 or a treatment gas 606, the inner housing is radiopaque and can comprise a radiation shield coating or be manufactured with radiation shield materials, the inner housing 108 having one or more of an aperture 120 disposed through the inner housing 108 to selectively allow radiation from the radiation source 602, the treatment drug 604, or the treatment gas 606 to be directionally released through one or more of the aperture 120 into the treatment site 204 during the treatment cycle.

An outer housing 104 is radiopaque and can comprise a radiation shield or be manufacture from radiation shielding materials, the outer housing 104, selectively having a one or more of an aperture 116 disposed through the outer housing 104, the outer housing 104 is positioned proximate to the inner housing 108.

A case 102 comprising, selectively a plurality of third apertures disposed through the case, the case 102 is radiation permeable and surrounds the inner housing 108 and outer housing 104, either the inner housing 108 is affixed to the case 102 and the outer housing 104 is slidable relative to the inner housing 108 or the outer housing 104 is affixed to the case 102 and the inner housing 108 is slidable relative to the outer housing 104. The inner housing 108 or the outer housing 104 is repositionable, blocking all or some of the inner housing 108 apertures 120 to control directionality and dosage of radiation 602 exposure, the treatment drug 604 delivery, or the treatment gas 606 delivery to the treatment site 202. The treatment drug 604 or the treatment gas 606 is released when at least one of the inner housing 108 apertures 120, at least one of the outer housing 104 apertures 116, and at least one of the case 102 apertures 128 are aligned allowing egress of the treatment drug 604 or the treatment gas 608 from the inner housing 108 into the treatment site 202.

This operation allows each radiation release capsule 100 seed to be turned "on" or "off" remotely depending on if the seed is located at the desired treatment site 202 location. The radiation shield and components such as the inner housing 108 and outer housing 104, are made of a material that has a high effective atomic number (Z) and a high physical density so that the X-rays emitted from the seed can be effectively absorbed via the photoelectric effect. It must also have the proper stiffness, strength, and malleability. One such candidate, for example, and not a limitation is a platinum-iridium (Pt/Ir) alloy made of 10% Pt and 90% Ir. It has an effective Z of 77.1 and a density of 22.4 g/cm$^3$, and has been successfully used as the wall material to encapsulate the californium-252 ($^{252}$Cf) source seed for neutron brachytherapy.

In an exemplary embodiment, a radiation release capsule can be designed and manufactured using computer-aided design (CAD) tools, 3D printing, integration with a controller 300, microcontroller 302, and an implantable antenna 306. CAD software tools can be used to design and create the inner housing 108 and outer housing 104 shielding with aperture openings on different sides and heights of the inner housing 108 and outer housing 104 to control the directivity of the radiation 602 and to completely shield the radiation emanating from the radiation source 602. Radiation release capsule 100 parts can be 3D printed using high resolution 3D printers including metal 3D printing and laser sintering 3D printing. The resolution depends on the scale and size of the device, which can be scaled to as small as 1 cm or less and as large as tens of centimeters, depending on the type and/or location of tumor, diagnosis, and treatment plan.

In an exemplary embodiment, for example and not a limitation, Pt/Ir alloy powder can be used to 3D print the radiation release capsule to shield X-ray radiation sources such as $^{125}$I, $^{103}$Pd, and $^{131}$Cs. Several companies, including American Elements and Heraeus Group provide 3D printing services of this Pt/Ir alloy powder as well as other custom alloy powders for novel compositions. A small microcontroller 302 with wireless communication capability such as the NRF52832-CIAA-R (dimensions of 3 mm×3 mm) can be integrated with electromagnet(s) and a permanent magnet to control the displacement of the outer shielding. The NRF52832 chip, for example, dissipates 0.3 µA in the OFF mode and 1.9 µA in the ON mode, and the power supply is 1.7V-3.6V, which gives a lot of flexibility in the choice of ultra-thin, small batteries. Many of these batteries are less than 0.5 mm in thickness and can last 6 months to over a year depending on the capacity. Besides, the NRF52832 other chips will be tested and compared in the research.

An implantable antenna 306 can be designed and connected to wireless communications interface 304 to remotely control the movement of the inner housing 108 or the outer housing 104 depending on which is slidably in a particular embodiment. Implantable antennas 306 have been a recent topic of research to enable remote control of implantable medical devices. The antenna can be designed for either near-field communication or far-field communication. Several frequency ranges have been suggested and are currently tested to be used in different medical implant applications. The antenna 306 designs can be based on the most widely used and common Medical Implant Communications Services (MICS), Wireless Medical Telemetry Service (WMTS), and Industrial, Scientific, and Medical (ISM) frequency bands. One of the design considerations and specifications is the device/antenna size and wireless range. Another design consideration is maintaining biocompatible insulation of the antenna, to avoid safety issues. There have been advances in materials for recent low-profile implantable bioelectronics, which include materials such as Parylene C and polydimethylsiloxane (PDMS) which are widely used as biocompatible insulation material for implanted electronics, which can be used as the biocompatible mesh 702 to fix the position of the device in place.

Different antenna 306 designs are possible for this application, including fractal or L-shaped fed spiral, meandered PIFA, loop antennas, and helical antennas. Table 1 shows the dimensions, design type, and frequency bands for the miniaturized, implantable antennas operating at MICS and ISM frequency bands.

TABLE 1

Dimensions and types of miniaturized implantable antennas at MICS and ISM frequency bands.

| Dimension (mm) | Design Type | Frequency Band |
| --- | --- | --- |
| 14 × 14 × 15 | Spiral | MICS |
| 15 × 15 | PIFA | ISM |
| 11.5 × 8 × 8 | Fractal Arc. Spirals | MICS |
| 15 × 4.5 | Helical | 868 MHz |
| 5.3 × 3.25 | Meandered PIFA | ISM |
| 0.16 | Loop antenna | 4 GHz |
| 15 × 15 × 1.92 | L- Shaped fed spiral | ISM, MICS |
| 14 × 14 | Magnetic-type loop | MICS |

Turning now to the drawings in greater detail, FIG. 1 illustrates one example of a system for remotely managing radiation release capsules 100. In an exemplary embodiment, a radiation release capsule 100 can be implanted or other positioned proximate a treatment site 204 within a treatment environment 202. A human body can be a treatment environment 202. Treatment environments can also include animal bodies, as well as other environments, as may be required and/or desired in a particular embodiment.

In operation a digital device 512A can be operated by authorized personnel 206 such as the manufacturer, medical professional, or other authorized personnel to wirelessly program the treatment cycle, program the radiation release capsule, monitor or adjust operation status of the radiation release capsule 100, or communicated other data with the radiation release capsule 100, as may be required and/or desired in a particular embodiment. The digital device 512A can also data communicate over a global communication network 500 with other data processing radiation release capsule including server 504, remote telemedicine professionals 208, other digital devices 512B, and/or other data process resources and digital devices, as may be required and/or desired in a particular environment. A global communication network 500 can be the Internet. A digital device 512A and 512B can be a smartphone such as an iPhone, Samsung Galaxy, HTC, or other types and kinds of smartphones, as may be required and/or desired in a particular embodiment. A digital device 512A and 512B can also be a tablet computer, a notebook computer, a laptop computer, a server, workstation, or other digital devices, as may be required and/or desired in a particular embodiment.

A digital device 512B can be operated by a person operator 210 such as the patient, the caregiver, an in-home medical professional, or other authorized personnel to wirelessly program the treatment cycle, program the radiation release capsule 100, monitor or adjust operational status of the radiation release capsule, or communicate other data with the radiation release capsule 100, as may be required and/or desired in a particular embodiment. The digital device 512B can also data communicate over a global communication network 500 with other data processing device including server 504, remote telemedicine professionals 208, other digital devices 512A, and/or other data process resources and digital devices, as may be required and/or desired in a particular environment. For purposes of disclosure, digital device 512A and 512B can be referred to as digital device 512. A safety feature of the present invention is to deny the person operator 210 from accessing or changing settings, programming feature, or treatment cycles, and other data associated with the radiation release capsule 100. However, a telemedicine professionals 208 or an authorized personnel 206, remotely, by way of the person operator 210 digital device 512B can effectuate such settings, programming feature, or treatment cycles, and other data associated with the radiation release capsule 100 changes.

In an exemplary embodiment, a person operator 210 can data communication over the global communication network 500 with remote telemedicine professionals 208. In this regard, the remote telemedicine professionals 208 by way of the digital device 512B can provide telemedicine services with the person operator 210. Such telemedicine services can include programming the treatment cycle, programming the radiation release capsule 100, monitor or adjust the operation status of the radiation release capsule, or communicating other data with the radiation release capsule 100, as may be required and/or desired in a particular embodiment.

Additionally, a server 504 having a microprocessor 514 can also comprise a database 502 and a memory 506. The server 504 can data communicate over the global communication network 500 with other data processing resources and digital devices, as may be required and/or desired in a particular embodiment. The memory 506 can be encoded with instructions that when executed by the server 506 microprocessor 514 effectuate various methods of the present invention.

Figure 2:
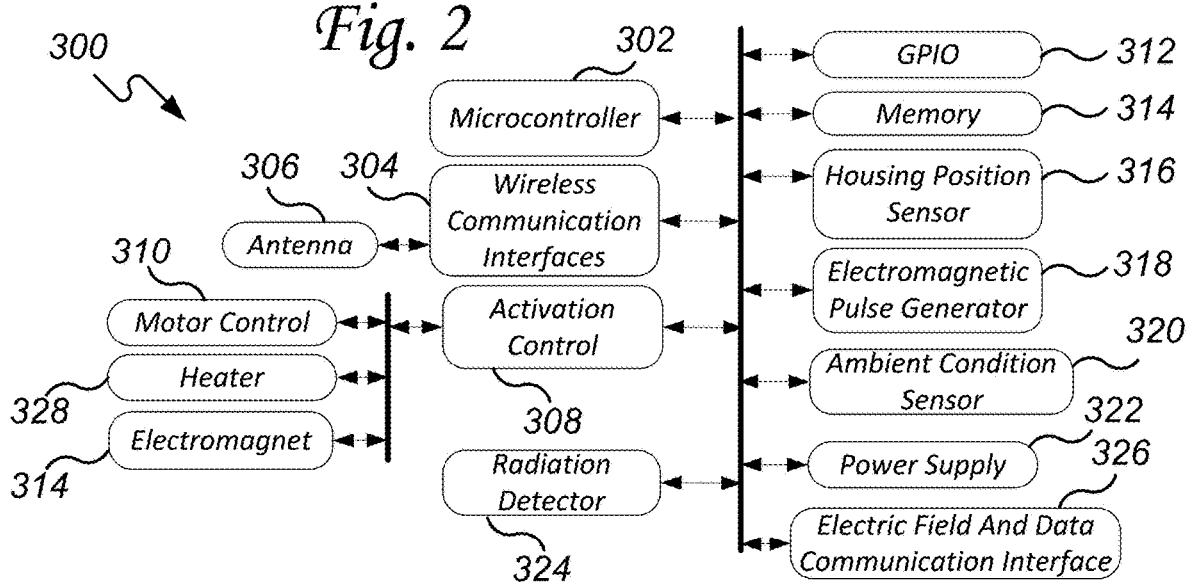
FIG. 2 illustrates one example of the controller system block diagram.

Referring to FIG. 2, there is illustrated one example of a controller 300 system block diagram. In an exemplary embodiment, controller 300 effectuates operation of radiation release capsule 100 as well as wireless communications with other proximate radiation release capsule 100 as wells as with digital devices 512 external the treatment environment 202. Controller 300 is integrated into the radiation release capsule 100 fitted into compartment 112.

A microcontroller 302 can be interconnected with and operationally related to a wireless communication interface 304, and general-purpose inputs and outputs (GPIO) 312 such as TTL, CMOS, transistor drivers, FET or MOSFET, or other types or kinds of GPIO. Furthermore, the microcontroller 302 can be connected with and operationally related memory internal to the microcontroller 302 or external to the microcontroller 302 collectively referred to as memory 314. Continuing, microcontroller 302 can be connected with and operationally related to an activation control 308, a housing position sensor 316, a radiation detector 324, an electromagnetic pulse generator 318, ambient condition sensors 320, or an electrical field and data connection interface 326. A power supply 322 can power the controller 300.

The wireless communication interface 304 can be interconnected with antenna 306. Antenna 306 can be integrated with a biocompatible mesh 702 which is better illustrated in at least FIGS. 4A and 4B. The antenna can be a far-field design such as illustrated in FIG. 4A, a near-field design such as illustrated in FIG. 4B, or other antenna design, as may be required and/or desired in a particular embodiment. In applications where the antenna 306 is integrated into the biocompatible mesh 702, the antenna is conductive and electrically insulated from the biocompatible mesh 702. In a plurality of other exemplary embodiments, the antenna 306 can be of any type of antenna, not limited to dipole antennas.

In an exemplary embodiment, the wireless communication interface can support Bluetooth, pico-network communication designs and protocols, mesh-network communication designs and protocols, Zigbee communication designs and protocols, Internet-of-Things (IoT) communication designs and protocols, common Medical Implant Communications Services (MICS), Wireless Medical Telemetry Service (WMTS), and Industrial, Scientific, Medical (ISM) frequency bands, and other wireless communication designs and protocols, as may be required and/or desired in a particular embodiment.

In an exemplary embodiment, an activation control 308 can be integrated with an electromagnet 314. In operation, the controller 300 by way of the activation control 308 can operate the electromagnet 314 to reposition either the inner housing 108 or the outer housing 104. In other exemplary embodiments, the activation control 308 can be interconnected with a motor control 310 for driving inductive loads that cause reposition of the inner housing 108 or the outer housing 104. The activation control 308 can also be interconnected with a heater 328 for nitinol wire applications, elastomer, and other applications where heating the wire, nitinol wire, or elastomer causes repositioning of the inner housing 108 or the outer housing 104. The activation control 308 can also be interconnected a shape-memory polymer. The activation control 308 can also be interconnected in other manners to effectuate repositioning of the inner housing 108 or the outer housing 104, as may be required and/or desired in a particular embodiment.

In an exemplary embodiment, the radiation detector 324 can be a PIN diode radiation detector such as manufactured by Microsemi Corp or other types and kinds of radiation detector diodes, devices, systems, or electronic components, as may be required and/or desired in a particular embodiment. Additionally, the radiation detector 324 can be integrated into the microcontroller 302 as a system-on-chip or other configuration. In operation, the radiation detector 324 can be used to read the radiation 602 level emanating from the radiation release capsule 100 and such reading can be used in the methods of the present invention to set a desired radiation 602 dosage amount by adjusting by unblocking, blocking, or partially blocking the aperture sizes in the inner housing 108 to deliver a desired radiation dosage amount for a prescribed treatment period to the treatment site. In other exemplary embodiment, the radiation detector 324 can be other types and kinds of radiation detecting devices, as may be required and/or desired in a particular embodiment.

In an exemplary embodiment, a housing position sensor 316 indicates the position of the outer housing 104 with respect to the inner house 108. Such data can be used to position the housings with respect to each other so that one or more of the apertures are open, closed, or partially open in accordance with the treatment plan. Such a housing position sensor 316 can be a mechanical micro-switch, a change in conductance or inductance with respect to certain locations or components on the radiation release capsule 100, an optical switch, a Hall effect device, or other types and kinds position sensors, as may be required and/or desired in a particular application. One example of forming a micro-switch can be when connector 106 and activation control 118 are "open" or "closed". In this regard, when connector 106 and activation control 118 are separated "open", as illustrated in at least FIG. 6A, the radiation release capsule 100 is in the "off" position, and when connector 106 and activation control 118 are touching "closed", in at least FIG. 6B, the radiation release capsule 100 is in the "on" position.

In an exemplary embodiment, an electromagnetic pulse generator 318 can be configured with an electromagnetic 314 to deliver neurological or cardiac stimuli during the treatment cycle.

In an exemplary embodiment, an ambient condition sensor 320 can detect treatment site temperature, pressures, oxygen level, heart pulse, hydration, images of the treatment site from a camera incorporated into the ambient condition sensor 320, and other types and kinds of ambient conditions associated with the treatment site and proximate the radiation release capsule 100 can be determined and data communicated externally to digital devices 512, as may be required and/or desired in a particular embodiment.

In an exemplary embodiment, power supply 322 can be battery, MEMS energy harvester devices, wirelessly rechargeable so that the battery can be recharged from time to time after the radiation release capsule has been placed and in operation at the treatment site from a location proximate but outside of the treatment site 204 and/or treatment environment 202, or other types and kinds of power supplies, as may be required and/or desired in a particular embodiment.

Referring to FIG. 3, there is illustrated one example of a biocompatible mesh 702 comprising a plurality of radiation release capsules 100 positioned and secured thereon. In an exemplary embodiment, a plurality of radiation release capsules 100A-D can be positioned and secured to a biocompatible mesh 702.

In an exemplary embodiment, with reference to navigation compass 704, illustrated in the figure a radiation release capsule 100A is position at the north end of the biocompatible mesh 702, and the radiation 602 is directed towards the south end of the biocompatible mesh 702. Radiation release capsule 100B is position at the west end of the biocompatible mesh 702 and radiation 602 is directed towards the east end of the biocompatible mesh 702. Radiation release capsule 100C is position at the east end of the biocompatible mesh 702 and radiation 602 is directed towards the west end of the biocompatible mesh 702. Radiation release capsule 100D is position at the south end of the biocompatible mesh 702 and radiation 602 is directed towards the north end of the biocompatible mesh 702. The directional radiation beams 602 can be orientated and controlled to shield radiation away from the heart, lungs, other organs, and healthy tissue and towards the treatment area 204 where tumors or residual cancer cells are located where the radiation 602 has a treatment benefit.

In this regard, the directionality of radiation 602 exposure and, selectively treatment drug 604 delivery or treatment gas 606 deliver can be orientated, spaced, and otherwise position and secured to the biocompatible mesh 702. The biocompatible mesh 702 can then be placed to the treatment site 204. The treatment site 204 can be a tumor, cancer, residual cancer cells, or other mass or cells requiring radiation treatment.

Referring to FIGS. 4A and 4B, there are illustrated examples of a biocompatible mesh 702 comprising an antenna 306. In an exemplary embodiment, the antenna 306 can be a far-field design such as illustrated in FIG. 4A, a near-field design such as illustrated in FIG. 4B, or other antenna design, as may be required and/or desired in a particular embodiment. The antenna 306 is conductive and electrically insulated from the biocompatible mesh 702.

Figure 5A:
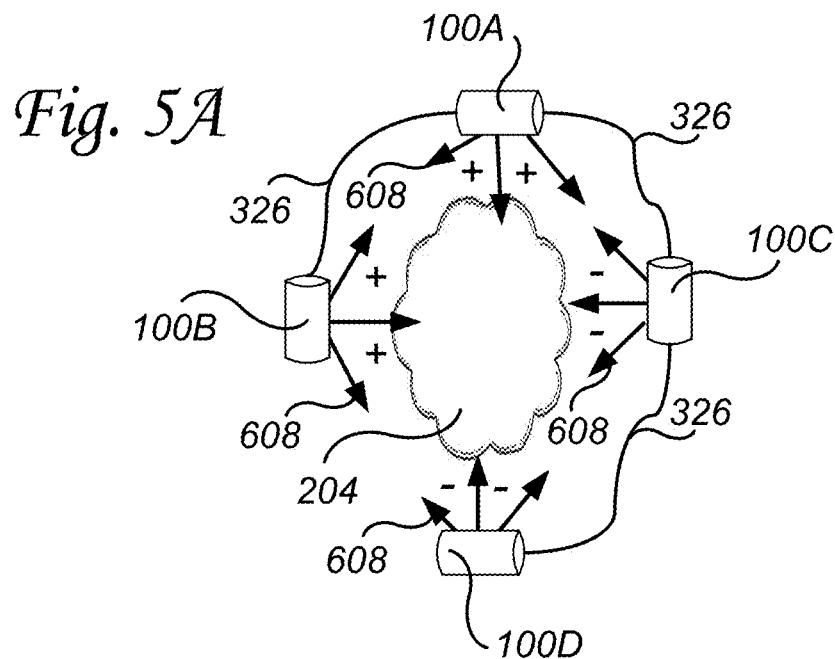
FIGS. 5A and 5B illustrate examples of electrical field therapy and electromagnetic pulse therapy.
Figure 5B:
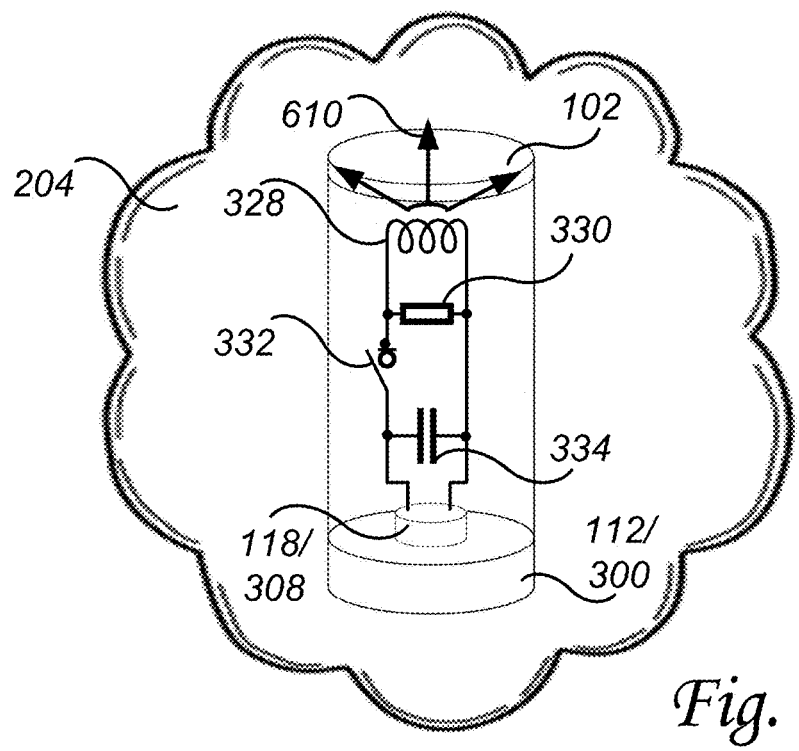

Referring to FIGS. 5A and 5B, there is illustrated examples of electrical field therapy and electromagnetic pulse therapy. In an exemplary embodiment, referring to FIG. 5A, a plurality of radiation release capsules 100A-D can be places around the treatment site 204. Interconnected, by way of electrical field and data connection interface 326, the radiation release capsules 100 can coordinate generating alternating and/or varying electrical fields 608 between the plurality of radiation release capsules 100A-D. The controller 300 can comprise the electrical field and data connection interface 326, and the electrical field and data connection interface 326. The memory 314 can be encoded with instructions that when executed by the microcontroller 302 perform the steps of delivering the alternating and varying electric field treatment across the treatment site 204.

In this regard, some of the radiation release capsules 100 can be switched to positive potential while others switch to negative potential to create and electrical field there between across the treatment site 204. Each of the radiation release capsules 100A-D can be switched to a positive or negative potential so electrical fields can continuously be alternated and varied across the treatment site 204. Such electric field treatment can disrupt cell mitosis preventing cells like cancer to slow, abate, or stop cell division and growth.

In operation, the electrical and data connections 326 effectuates the ability of the plurality of radiation release capsules 100A-D to synchronize which of the capsules 100A-D will switch to positive potential and which will switch to negative potential to create the electrical. Data and power can be exchanged across the electrical and data connections 326 to synchronize the radiation release capsule 100A-D activities, as may be required and/or desired in a particular embodiment. As prescribed, the treatment plans can include a combination of directed radiation dosing from the plurality of radiation release capsules 100A-D to the treatment site 204 as well as electric field therapy.

In an exemplary embodiment, referring to FIG. 5B, there is illustrated electromagnetic pulse therapy. In an exemplary embodiment, the electromagnetic pulse generator 318 comprises a capacitor 334 for storing energy, a resistor 330, a switch 332, and an inductor 328 that creates a magnetic field surge when the capacitor 334 is charged with the switch 332 open and then the switch 332 is closed discharging the capacitor 334. In this exemplary embodiment, the case 102, the inner housing 108, and the outer housing 104 should be non-conductive. The inductive loop can be a single conductive loop, multiple conductive loops, conductive loops with ferromagnet materials to increase the magnetic field strength, or other types and kinds of conductive loops, as may be required and/or desired in a particular embodiment. The capacitor 334 can be a super capacitor, or other types and kinds of capacitors or energy storage devices, as may be required and/or desired in a particular embodiment. The resistor 330 can be a digital potentiometer to control circuit damping. As prescribed, the treatment plans can include a combination of directed radiation dosing from the plurality of radiation release capsules 100A-D to the treatment site 204 as well as electromagnetic pulse therapy.

In operation, controller 300, by way of the electromagnetic pulse generator 318 charges or otherwise stores energy in the capacitor 334. The capacitor 334 can be partially or fully charged to control the intensity of the electromagnetic pulse. Once charged, the switch is closed and the stored energy is delivered through the inductor 328 creating the electromagnetic pulse. The controller 300 controls the charging of the circuit, including the charging rate and charge amount, as well as the opening and closing of the switch 332. In this regard, the controller 300 controls the electromagnetic pulse intensity and pulse rate, and as such delivers the prescribed pulse treatment to the treatment site 204 in accordance with the treatment plan. The switch can be a MOSFET, relay, or other type and kind of switch, as may be required and/or desired in a particular embodiment.

Electromagnetic pulse therapy, also known as pulsed electromagnetic field therapy is often abbreviated as PEMF therapy. With a proven track record of over decades of success demonstrated by myriad research studies and clinical trials, PEMFs are a valuable therapeutic tool for a wide range of health conditions.

First approved by the Federal Drug Administration (FDA) in 1979 for use in healing nonunion fractures, PEMF therapy has since been approved for a number of other applications, including treatment of urinary incontinence, treatment of cervical fusion patients at high risk of non-fusion, treatment of depression and anxiety, and treatment of brain cancer.

Furthermore, PEMF has been shown to improve migraines, back pain, joint problems, swelling, skin wound healing, lack of circulation, arthritis, fibromyalgia, and more. PEMF has also been found to improve pain often associated with soft tissue injuries, including cervical neck pain, epicondylitis (tennis elbow), sprains, strains, repetitive strain injuries, carpal tunnel syndrome, tendinopathies, and plantar fasciitis.

The key mechanism in electromagnetic pulse therapy is the magnetic pulses that create a healing effect proximate the treatment site 204 and throughout the treatment environment 202. The outcome of this therapy is an increased range of motion, less swelling, and less pain in the afflicted areas.

Referring to FIGS. 6A, 6B, and 6C, there is illustrated one example of the radiation release capsule 100 having an activation control 118 and operating turn "on" and "off" radiation exposure at a treatment site 204.

In an exemplary embodiment, FIG. 6A illustrates the radiation release capsule 100 aperture 116 in the outer housing 104 misaligned with the aperture 120 in the inner housing 108 shielding the radiation source 602 stored in a cavity within the inner housing 108, and selectively treatment drugs 604 or treatment gases 606 also stored within the inner housing from being released into the treatment site 204 when the activation control 118/308 is an electromagnet 314 and the electromagnet 314 is deactivated. Connector 106 is secured to either the inner housing 108 or the outer housing 104. Connector 106 can be a permanent magnet and use magnetism to return the radiation release capsule 100 to radiation sealed and turned "off" safe state where the inner housing 108 aperture 120 is closed or blocked by the outer shield 104 preventing radiation from emanating from the radiation release capsule 100 when the electromagnet 314 is deactivated. Controller 300 is integrated into the radiation release capsule 100 fitted into compartment 112 and operates the radiation release capsule 100. Either the inner housing 108 or the outer housing 104 is affixed to the case 102 by fastener 122 allowing the unaffixed housing to move relative to the fixed housing. Such a fastener can be a permanent magnet, adhesive, weld, or other fastening mechanisms, as may be required and/or desired in a particular embodiment. The case 102, selectively can have one or more aperture 128 configured for the purpose of allowing treatment drugs 604 or treatment gas 606 to egress the radiation release capsule when the inner housing 108 aperture 120, the outer housing 104 aperture 116, and the case 102 aperture 128 are aligned.

FIG. 6B illustrates the radiation release capsule 100 aperture 116 and 120 between the inner housing 108 and outer housing 104 aligned allowing radiation from the radiation source 602 and, selectively treatment drugs 604 or treatment gases 606 to be released into the treatment site 204 from the radiation release capsule 100 when the activation control 118/308 is an electromagnet 314 and the electromagnet 314 is energized and activated.

FIG. 6C illustrates the radiation release capsule 100 apertures 116 and 120 between the inner housing 108 and outer housing 104 misaligned shielding the radiation source 602, treatment drugs 604, or treatment gases 606 from being released into the treatment site 204 when the activation control is an activation control 118 activated by motor control 310 or heater 328 and the activation control 118 is deactivated.

In operation, one of the outer housing 104 or the inner housing 108 is fixed by fastener 122 to case 102 the other housing is movable. The controller 300 by way of electromagnet 314 is used to pull or push the movable housing to open aperture 120 when apertures 116 and 120 are aligned and close aperture 120 when apertures 116 and 120 are misaligned. The controller 300 can be programmed so that dosage incidence, duration, and the amount can be pre-programmed for some length of time (days, weeks, months) until the energy in the radiation 602 pellets is depleted.

Referring to FIGS. 6A, 6B, and 6C, there is illustrated one example a radiation release capsule 100 regulating the radiation 602 exposure at a treatment site 204 by controlling the aperture 120 opening in the inner housing 108 to be either open providing access to the inner housing 108 cavity allowing radiation 602 exposure to the treatment site 204, closed preventing access to the inner housing 108 cavity preventing radiation 602 exposure to the treatment site 204, or partly open where apertures 120 in the inner housing and 116 in the outer housing slightly overlap allowing partial radiation 602 exposure to the treatment site 204.

In an exemplary embodiment, FIG. 7A illustrates the radiation release capsule 100 holding a radiation source 602 and, selectively treatment drug 604 or treatment gas 606 where the radiation, the treatment drug, or the treatment gas is shielded from a release by the outer housing 104. Connector 106 can be a permanent magnet and use magnetism to return the radiation release capsule 100 to a safe state where the inner housing 108 aperture 120 is closed or block by the outer shield 104 preventing radiation from emanating from the radiation release capsule 100 when the electromagnet 314 is deactivated. Controller 300 is integrated into the radiation release capsule 100 fitted into compartment 112 and operates the radiation release capsule 100. Either the inner housing 108 or the outer housing 104 is affixed to the case 102 by fastener 122 allowing the unaffixed housing to move relative to the fixed housing. Such a fastener can be a permanent magnet, adhesive, weld, or other fastening mechanisms, as may be required and/or desired in a particular embodiment.

FIG. 7B illustrates one example of the radiation release capsule holding a radiation source 602 and, selectively treatment drug 604, or treatment gas 606 where the outer shell 104 has been repositioned so that the aperture 120 in the inner housing 108 and aperture 116 on the outer housing 104 partially align so that some radiation 602 and, selectively some of the treatment drug 604 or some of treatment gas 606 is released from the radiation release capsule 100.

FIG. 7C illustrates one example of the radiation release capsule 100 holding a radiation source 602 and, selectively treatment drug 604 or treatment gas 606 where the outer shell 104 is repositioned so that the aperture 120 in the inner housing 108 and aperture 116 in the outer housing 104 align releasing that maximum amount of radiation 602 and, selectively the treatment drug 604 or the treatment gas 606 from the radiation release capsule 100.

In operation, one of the outer housing 104 or the inner housing 108 is fixed by fastener 122 to case 102 the other housing is movable. The controller 300 by way of electromagnet 314 is used to pull or push the movable housing to open aperture 120 when apertures 116 and 120 are aligned, close aperture 120 when apertures 116 and 120 are misaligned, or partially open aperture 120 when apertures 116 and 120 are partially aligned. The controller 300 can be programmed so that dosage incidence, duration, and the amount can be pre-programmed for some length of time (days, weeks, months) until the energy in the radiation 602 pellets is depleted.

In an exemplary embodiment, a radiation release capsule for controlling radiation exposure and selectively delivering treatment drugs or treatment gases at a treatment site associated with a treatment environment in accordance with a treatment cycle.

The radiation release capsule 100 can comprise an inner housing 108 that is radiopaque, the inner housing 108 defines a cavity configured to at least encompass a radiation source 602. The inner housing 108 having one or more of an aperture 120 disposed through the inner housing to allow radiation from the radiation source 602 to be directionally released during the treatment cycle. An outer housing 104 is radiopaque and positioned proximate the inner housing 108. A case 102 is radiation permeable and surrounds the inner housing 108 and outer housing 104. Either the inner housing 108 is stationary and the outer housing 104 is slidable relative to the inner housing 108 or the outer housing 104 is stationary and the inner housing 108 is slidable relative to the outer housing 104 to control directionality and dosage of the radiation delivered to the treatment site by unblocking, blocking, or partially blocking the aperture 120.

A controller 300 comprising a microcontroller 302, a memory 314, and an activation control 308. The activation control 308 can be configured to slidably position either the inner housing 108 or the outer housing 104 by way of an electromagnet 314. Alternatively, the activation control 308 can be configured to slidably position either the inner housing 108 or the outer housing 104 by way of a nitinol wire, a wire, an elastomer, or a shape-memory polymer.

The memory 314 can be encoded with instructions that when executed by the microcontroller 302 perform the following steps of: receiving the treatment cycle from a digital device 512, by way of a wireless communication interface 304. The controller 300 comprises the wireless communication interface 304. The treatment cycle, by way of the controller 300, effectuates delivery of a desired radiation dosage amount for a prescribed treatment period by transitioning between: exposing, by slidably positioning the outer housing 104 or the inner housing 108 so that at least portion of the aperture 120 is unblocked by the outer housing engendering radiation delivery to the treatment site. And blocking the aperture 120, with the outer housing 104, preventing radiation delivery to the treatment site 204.

The memory 314 can be encoded with instructions that when executed by the microcontroller 302 perform the step of: communicating data or intelligent signals between the wireless communication interface 304 and co-located other of the radiation release capsule 100 or the digital device 512 related to at least one of the following: the treatment cycle, the treatment site, the radiation release capsule 100, or the radiation release capsule 100 operational status.

The memory can be encoded with instructions that when executed by the microcontroller perform the step of: determining the position of the outer housing 104 relative to the inner housing 108 by way of a housing position sensor 316. The controller 300 comprising the housing position sensor 316.

A biocompatible mesh 702 configured to receive one or more of the radiation release capsule 100. The biocompatible mesh 702 affixing the orientation of the radiation release capsule relative to the biocompatible mesh 702. The biocompatible mesh 702 is securable proximate the treatment site and prevents disorientation or migration of the radiation release capsule during the treatment cycle. An antenna 306 is operationally related to a wireless communication interface 304. The controller 300 comprising the wireless communication interface 304.

An electromagnetic pulse generator 318 can be configured to provide neurological or cardiac stimuli during the treatment cycle. The controller 300 further comprising the electromagnetic pulse generator 318.

Referring to FIGS. 7A, 7B, 7C, and 7D, there is illustrated one example of the inner housing having varied size apertures to vary the radiation exposure dosage and, selectively deliver treatment drugs or treatment gases at a treatment site.

Figure 8A:
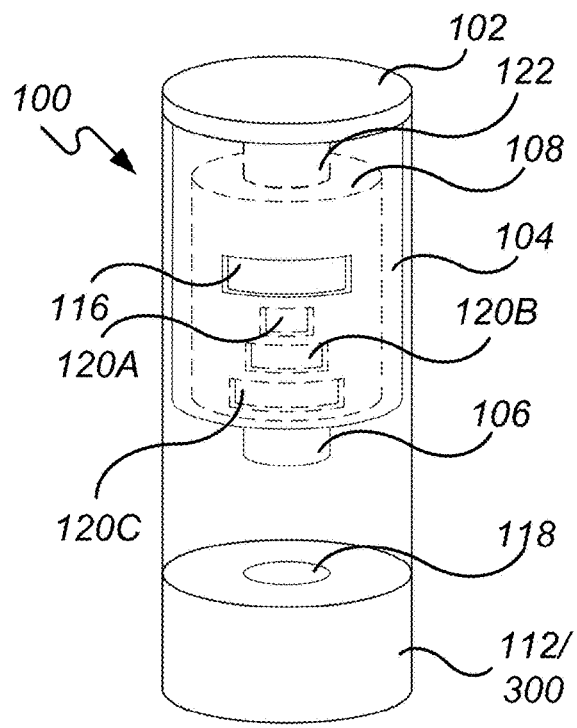
FIGS. 8A, 8B, 8C, and 8D illustrate one example of the inner housing having varied size apertures to vary the radiation exposure dosage and selectively deliver treatment drugs or treatment gases at a treatment site.

In an exemplary, FIG. 8A illustrates a shielded radiation release capsule 100 state where radiation from a radiation source 602 and, selectively treatment drug 604 or treatment gas 604 are not released from the radiation release capsule 100. Inner housing 108 apertures 120A, 120B, and 120C are blocked by outer housing 104. Connector 106 is secured to either the inner housing 108 or the outer housing 104. Connector 106 can be a permanent magnet and use magnetism to return the radiation release capsule 100 to a safe state where the inner housing 108 aperture 120 is closed or block by the outer shield 104 preventing radiation from emanating from the radiation release capsule 100 when the electromagnet 314 is deactivated. Controller 300 is integrated into the radiation release capsule 100 fitted into compartment 112 and operates the radiation release capsule 100. Either the inner housing 108 or the outer housing 104 is stationary or otherwise affixed to the case 102 by fastener 122 allowing the unaffixed housing to move relative to the fixed housing. Such a fastener can be a permanent magnet, adhesive, weld, or other fastening mechanisms, as may be required and/or desired in a particular embodiment.

Figure 8B:
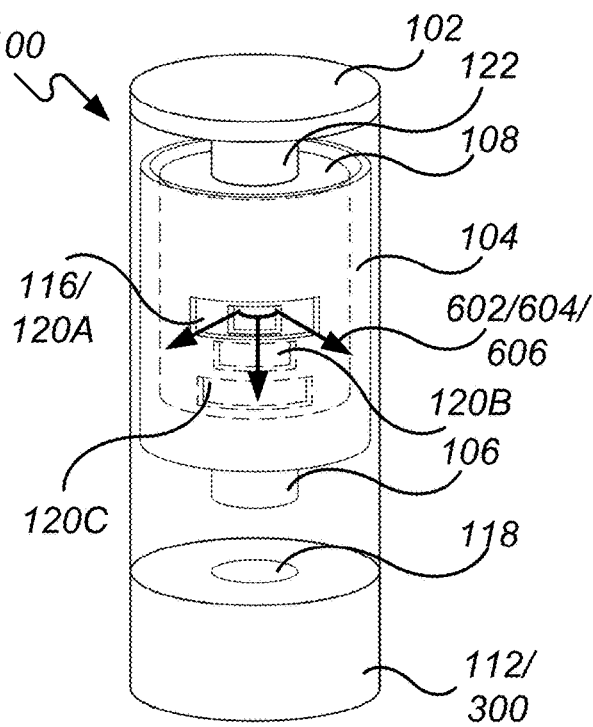

FIG. 8B illustrates a small radiation release capsule 100 radiation 602 release state where a minimal radiation 602 exposure dosage, a minimal treatment drug 604 delivery, or minimal treatment gas 606 delivery is released from the radiation release capsule 100 to the treatment site 204 when outer housing 104 aperture 116 is positioned over inner housing 108 smaller size aperture 120A.

Figure 8C:
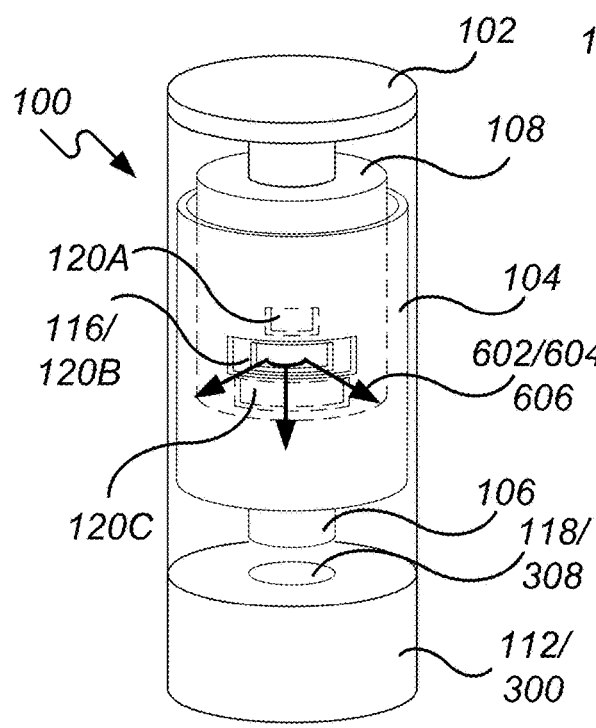

FIG. 8C illustrates a medium radiation release capsule 100 release radiation 602 release state where a medium radiation 602 exposure dosage, a medium treatment drug 604 delivery, or medium treatment gas 606 delivery is released from the radiation release capsule 100 to the treatment site 204 when outer housing 104 aperture 116 is positioned over inner housing 108 medium size aperture 120B.

Figure 8D:
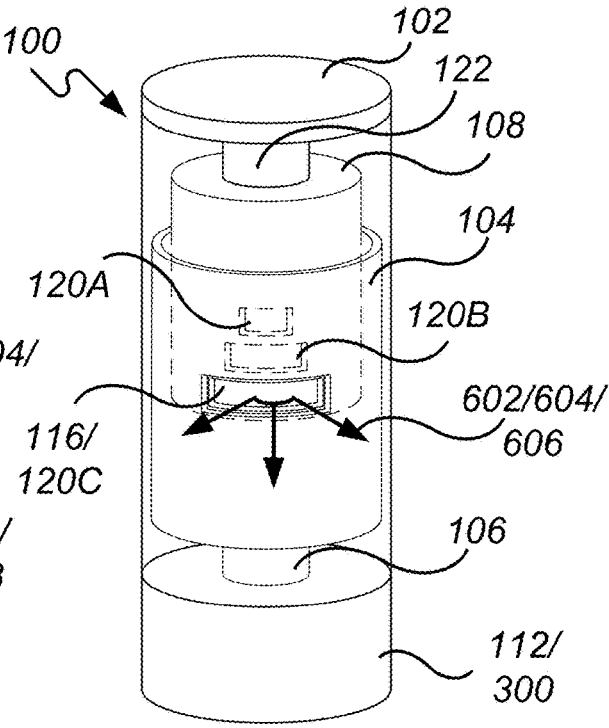

FIG. 8D illustrates a maximum radiation release capsule 100 release radiation 602 state where a maximum radiation 602 exposure dosage, a maximum treatment drug 604 delivery, or maximum treatment gas 606 delivery is released from the radiation release capsule 100 to the treatment site 204 when outer housing 104 aperture 116 is positioned over inner housing 108 maximum size aperture 120C.

In operation, one of the outer housing 104 or the inner housing 108 is stationary or otherwise fixed by fastener 122 to case 102 the other housing is movable. The controller 300 by way of electromagnet 314 is used to pull or push the movable housing to open at least one of apertures 120A, 120B, or 120C when at least one of those apertures are aligned with aperture 116 and close apertures 120A, 120B, or 120C when those apertures are misaligned with aperture 116. The controller 300 can be programmed so that dosage incidence, duration, and the amount can be pre-programmed for some length of time (days, weeks, months) until the energy in the radiation 602 pellets is depleted.

In an exemplary embodiment, a radiation release capsule 100 for controlling radiation exposure and selectively delivering treatment drugs or treatment gases at a treatment site associated with a treatment environment in accordance with a treatment cycle. The radiation release capsule comprising an inner housing that is radiopaque. The inner housing defines a cavity configured to at least encompass a radiation source 602. The inner housing having one or more of an aperture 120 disposed through the inner housing 104 to allow radiation from the radiation source 602 to be directionally released during the treatment cycle. an outer housing is radiopaque and positioned proximate the inner housing 108.

A case 102 is radiation permeable and surrounds the inner housing 108 and outer housing 104, either the inner housing 108 is stationary and the outer housing 104 is slidable relative to the inner housing 108 or the outer housing 104 is stationary and the inner housing 108 is slidable relative to the outer housing 104 to control directionality and dosage of radiation delivered to the treatment site by unblocking, blocking, or partially blocking the aperture 120.

A controller comprising a microcontroller 302, a memory 314, a radiation detector 324, a wireless communication interface 304, and an activation control 308, is configured to slidably position either the inner housing 108 or the outer housing 104. The memory 314 is encoded with instructions that when executed by the microcontroller 302 perform the following steps of receiving the treatment cycle from a digital device 512, by way of a wireless communication interface 304. The controller 300 can comprise the wireless communication interface 304. The treatment cycle, by way of the controller, effectuates delivery of a desired radiation dosage amount for a prescribed treatment period to the treatment site by transitioning between: exposing, by slidably repositioning the outer housing or the inner housing so that at least portion of the aperture is unblocked by the outer housing engendering radiation delivery to the treatment site, reading a radiation level by way of the radiation detector, comparing the radiation level to the desired radiation dosage amount, and adjusting the radiation level to match the desired radiation dosage amount by slidably repositioning the outer housing or the inner housing to increase or decrease the radiation level accordingly. Wherein returning to the step of reading until the prescribed treatment period is complete, and blocking the aperture, with the outer housing, preventing radiation delivery to the treatment site.

Data or intelligent signals can be communicated between the wireless communication interface and co-located other of the radiation release capsule or the digital device related to at least one of the following: the treatment cycle, the treatment site, the radiation release capsule, or the radiation release capsule operational status.

Referring to FIGS. 8A, 8B, and 8C, there is illustrated one example of radiation 602, treatment drug 604, or treatment gas 606 directivity control by having a plurality of apertures 120A, 120B, and 120C located on different sides and at different heights on the inner housing and outer housing.

In an exemplary embodiment, FIG. 9A illustrates a plurality of apertures 120A, 120B, and 120C disposed through the inner housing 108 in different orientations and locations. In a plurality of exemplary embodiment, any number of apertures, aperture sizes, and aperture locations can be disposed through the inner housing, as may be required and/or desired.

FIG. 9B illustrates the inner housing 108 and outer housing 104 fitted together having inner housing 108 apertures 120A, 120B, and 120C misaligned with outer housing 104 apertures 116A, 116B, and 116C shielding the radiation source within the inner housing 108 from emanating radiation 602 into the treatment site 204, and a thin-film radiation detector, that includes some of the sensing parts of radiation detector 324, covers the aperture 116 of the outer housing 104 when there is a misalignment between the inner 108 and outer 104 housing, and there is minimal to no radiation emission.

FIG. 9C illustrates the inner housing 108 and outer housing 104 fitted together having inner housing 108 apertures 120A, 120B, and 120C aligned with outer housing 104 apertures 116A, 116B, and 116C allowing the eradiation source within the inner housing 108 to emanate radiation 602 into the treatment site 204, and where the thin film radiation detector, that includes some of the sensing parts of radiation detector 324, are directly exposed to the radiation and can detect the direction of radiation and dose level depending on the degree of alignment between the inner and outer housing.

Referring to FIGS. 9A, 9B, and 9C, there is illustrated one example of an interlocking inner housing 108 having a plurality of rails 124 and an outer housing 104 having a plurality of grooves 126. In an exemplary embodiment, the inner housing 108 can be slidably fix from rotating with respect to the outer housing 116 by the inclusion of at least one of a rail 124.

Figure 10A:
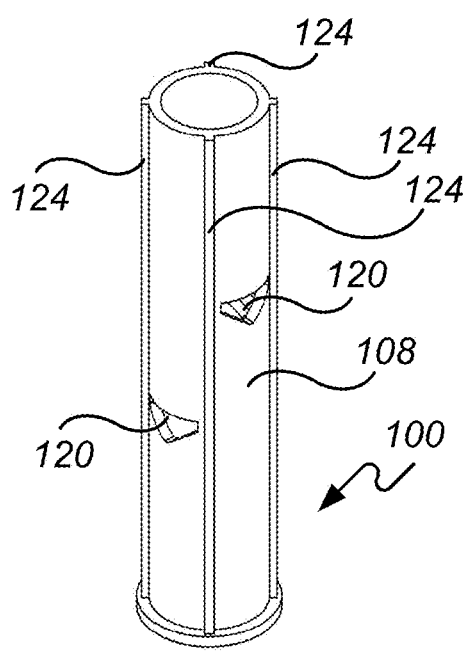
FIGS. 10A, 10B, and 10C illustrated one example of an interlocking inner housing having a plurality of rails and an outer housing having a plurality of grooves.
Figure 10B:
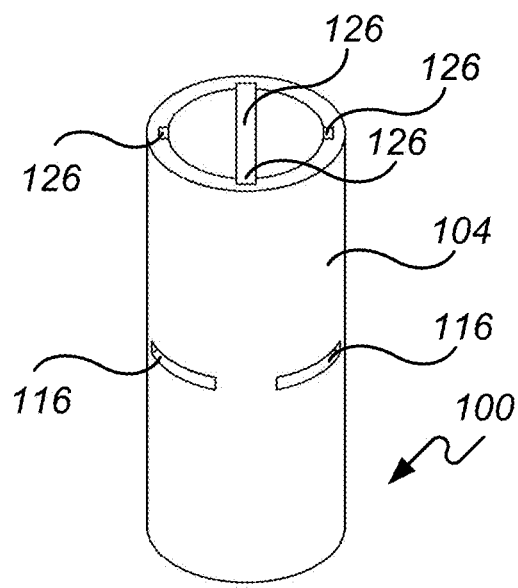
Figure 10C:
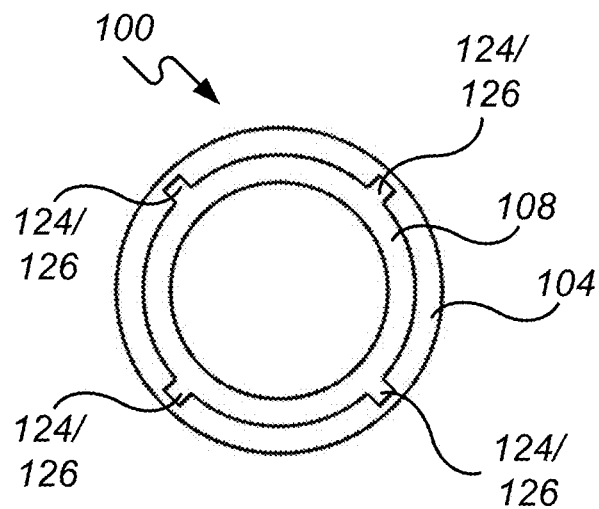

In this regard, FIG. 10A illustrates the rail 124 disposed along the surface of the inner housing 108. FIG. 10B illustrates how complimentary one or more of a groove can be disposed on the inner surface of the outer housing 104. FIG. 10C illustrates how the inner housing 108 and the outer housing 104 can be fitted together interlocking the rails 124 and grooves 126 so that the inner housing 108 can be slidably fix from rotating with respect to the outer housing 116.

Shielding can be of any shape, including a circular, oval, square, or rectangular cylinder or sphere or other shapes. The shielding material will have openings of any shape or size through which radiation can be emitted.

In an exemplary embodiment, in operation, a method of controlling radiation exposure and selectively delivering treatment drugs or treatment gases at a treatment site associated with a treatment environment in accordance with a treatment cycle can be effectuated by positioning one or more of a radiation release capsule 300 to the treatment site. The radiation release capsule can comprise a controller 300, an outer housing 104 that is radiopaque and an inner housing 108 that is radiopaque. The inner housing 104 defines a cavity configured to at least encompass a radiation source 602, the inner housing 108 having one or more of an aperture 120 disposed through the inner housing 108 to allow radiation from the radiation source 602 to be directionally released during the treatment cycle. The outer housing 104 can be positioned proximate the inner housing 108.

A case 102 is radiation permeable and surrounds the inner housing 108 and outer housing 104. Either the inner housing 108 is stationary and the outer housing 104 is slidable relative to the inner housing 108 or the outer housing 104 is stationary and the inner housing 108 is slidable relative to the outer housing 104 to control directionality and dosage of radiation delivered to the treatment site by unblocking, blocking, or partially blocking the aperture 120.

The treatment cycle can be delivered by way of the controller 300. The controller 300 can comprise a microcontroller 300, a memory 314, and an activation control 308. The activation control 308 is configured to slidably reposition either the inner housing 108 or the outer housing 104. The memory 314 is encoded with instructions that when executed by the microcontroller 302 perform the following steps of transitioning between: exposing, by slidably repositioning the outer housing 104 or the inner housing 108 so that at least portion of the aperture 120 is unblocked by the outer housing 104 engendering radiation delivery to the treatment site, and blocking the aperture 120, with the outer housing, preventing radiation delivery to the treatment site.

The treatment cycle can be received from a digital device 512, by way of a wireless communication interface 304. The controller 300 can comprises the wireless communication interface 304. Data or intelligent signals can be communicated between the wireless communication interface 304 and co-located other of the radiation release capsules 100 or a digital device 512 related to at least one of the following: the treatment cycle comprising a desired radiation dosage amount for a prescribed treatment period, the treatment site, the radiation release capsule, or the radiation release capsule 100 operational status.

A plurality of ambient conditions can be determined proximate the treatment site 204, by way of an ambient condition sensor 320, the controller 300 comprises the ambient condition sensor 320.

One or more of the radiation release capsule 100 can be secured to a biocompatible mesh 702, the biocompatible mesh 702 affixing the orientation of the radiation release capsule 100 relative to the biocompatible mesh 702, the biocompatible mesh 702 is secured proximate the treatment site preventing disorientation or migration of the radiation release capsule 100 during the treatment cycle.

Figure 11:
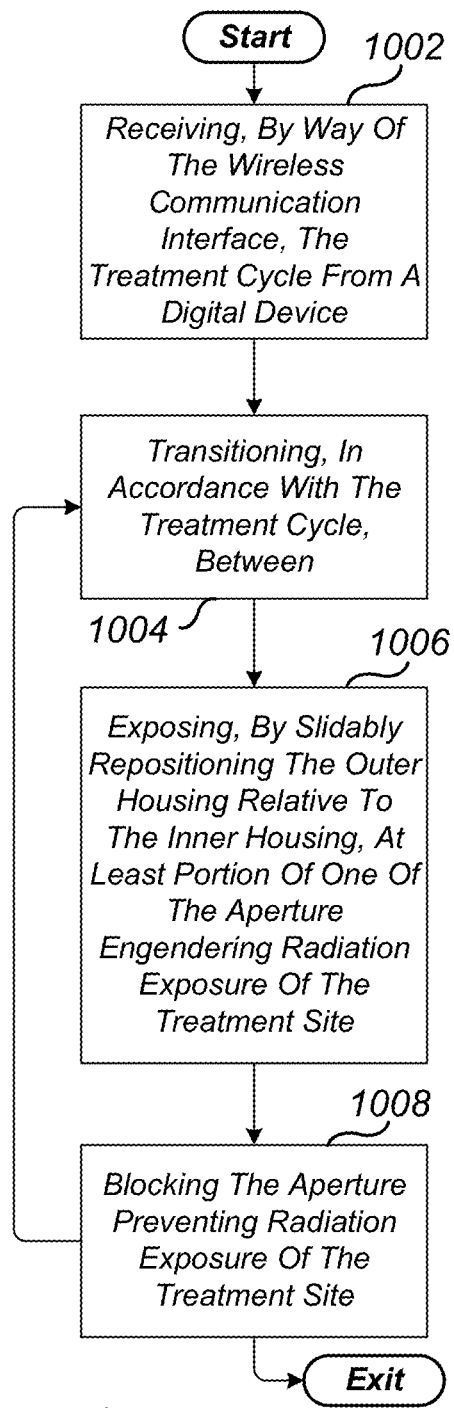
FIGS. 11, 12, and 13 illustrate example methods controlling radiation exposure and selectively delivering treatment drugs or treatment gases at a treatment site associated with a treatment environment in accordance with a treatment cycle.

Referring to FIG. 11, there is illustrated one example of a method of controlling radiation exposure and selectively delivering treatment drugs or treatment gases at a treatment site associated with a treatment environment in accordance with a treatment cycle. In an exemplary embodiment, an inner housing 108 defines a cavity is configured to at least encompass a radiation source 602 and, selectively a treatment drug 604 or a treatment gas 606.

The inner housing 108 is radiopaque and can comprise a radiation shield disposed as a coating on the surface of the inner housing 108 or the inner housing 108 is manufactured from radiation shielding material. The inner housing 108 has one or more of an aperture 120 disposed through the inner housing 108 to selectively allow radiation from the radiation source 602, the treatment drug 604, or the treatment gas 606 to be directionally released through one or more of the aperture 120 during the treatment cycle.

An outer housing 104 is radiopaque and can comprise a radiation shield disposed as a coating on the surface of the outer housing 104 or the outer housing 104 is manufactured from radiation shielding material. The outer housing 104, selectively has one or more of an aperture 116 disposed through the outer housing 104. The outer housing is positioned proximate to the inner housing.

A case 102 comprises, selectively a plurality of apertures disposed through the case 102. Case 102 is radiation permeable and surrounds the inner housing 108 and outer housing 104. Either the inner housing 108 is affixed to the case 102 and the outer housing 104 is slidable relative to the inner housing 108 or the outer housing 104 is affixed to the case 102 and the inner housing 180 is slidable relative to the outer housing 104. The inner housing 108 or the outer housing 104 is repositionable, blocking all or some of the inner housing 108 aperture 120 to control directionality and dosage of radiation exposure 602 and, selectively the treatment drug delivery 604, or the treatment gas 606 delivery to the treatment site 204. The treatment drug 604 or the treatment gas 606 is released when inner housing 108 aperture 120, the outer housing aperture 116, and the case 102 aperture 128 are aligned allowing egress of the treatment drug 604 or the treatment gas 606 from the inner housing 108 into the treatment site 204.

A controller 300 comprises a microcontroller 302, a memory 314, and a wireless communication interface 304. An electromagnet 314 is interconnected with an activation control 308. The activation control 308 operates an electromagnet 314, the memory 314 is encoded with instructions that when executed by the microcontroller 302 effectuates the method which begins in block 1002.

In this regard, in block 1002, the treatment cycle is received from a digital device 512 by way of the wireless communication interface. The treatment cycle comprises a plurality of opening and closing periods for certain of the inner housing 108 aperture 120 over a predetermined time period controlling radiation, from the radiation source 602, directionality and exposure dosage and, selectively treatment drug delivery 604 or treatment gas 606 delivery to the treatment site 204. The method moves to block 1004.

In block 1004, in accordance with the treatment cycle, the radiation release capsule 100 transitions between block 1006 and block 1008.

In this regard, in block 1006, at least a portion of one of the inner housing 108 aperture 120 is exposed and not blocked by the outer housing 104, by slidably repositioning the outer housing 104 or the inner housing 108 engendering radiation exposure, from the radiation source 602 and, selectively the treatment drug delivery 604 or other treatment gas 606 delivery to the treatment site 204. The electromagnet 314 is used to reposition either the inner housing 108 or the outer housing 104. The method moves to block 1008.

In block 1008, the inner housing 108 aperture 120 is blocked, with the outer housing 104, preventing radiation exposure, from the radiation source 602 and, selectively the treatment drug release 604, or the treatment gas 606 release to the treatment site 204, by deactivating the electromagnet 314. The method can return to block 1004 until the treatment cycle is complete and then the method is exited.

Figure 12:
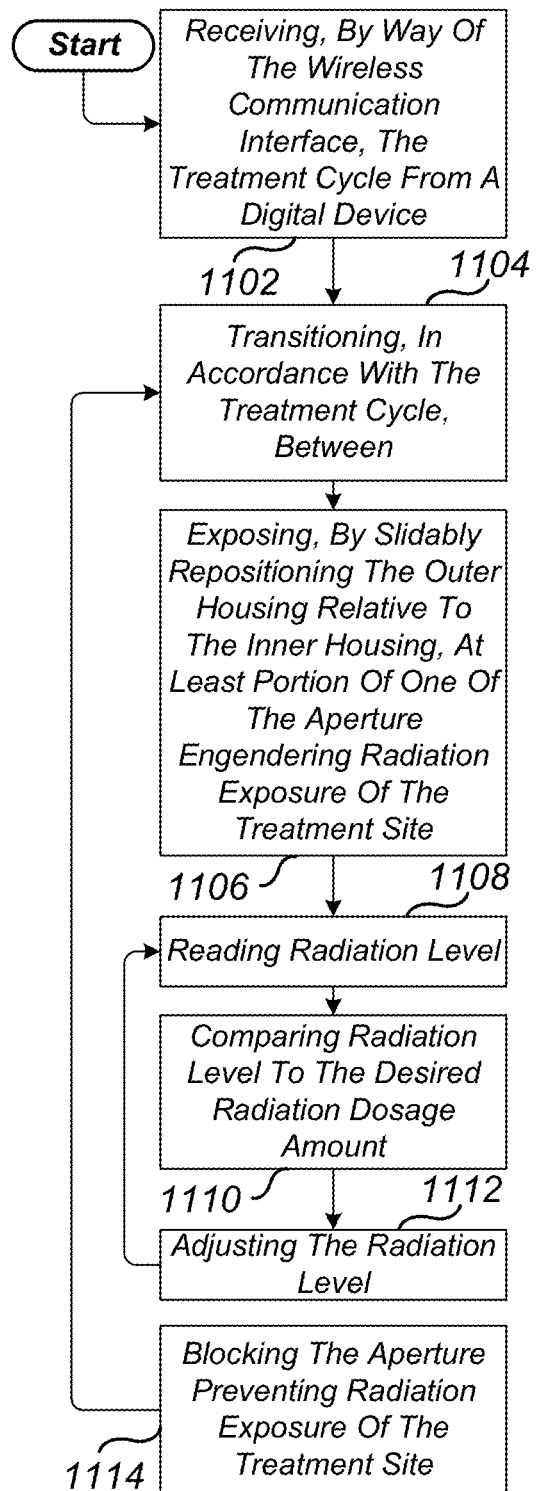

Referring to FIG. 12, there is illustrated one example of a method of controlling radiation exposure and selectively delivering treatment drugs or treatment gases at a treatment site associated with a treatment environment in accordance with a treatment cycle.

In an exemplary embodiment, an inner housing 108 defines a cavity configured to at least encompass a radiation source 602 and, selectively a treatment drug 604, or a treatment gas 606, the inner housing 108 is radiopaque and can comprise a radiation shield disposed as a coating on the surface of the inner housing 108 or the inner housing 108 is manufactured from radiation shielding material. The inner housing 108 having more than one of an aperture 120 disposed through the inner housing to selectively allow radiation from the radiation source 602 and, selectively the treatment drug 604 or the treatment gas 602 to be directionally released through one or more of the inner housing 108 apertures 120 during the treatment cycle.

An outer housing 104 is radiopaque and can comprise a radiation shield disposed as a coating on the surface of the outer housing 104 or the outer housing 104 is manufactured from radiation shielding material. The outer housing 104, selectively having one or more of an aperture 116 disposed through the outer housing 104. The outer housing 104 is positioned proximate to the inner housing 108.

A case 102 comprises, selectively a plurality of apertures 128 disposed through the case, the case 102 is radiation permeable and surrounds the inner housing 108 and outer housing 104. Either the inner housing 108 is affixed to the case 102 and the outer housing 104 is slidable relative to the inner housing 108 or the outer housing 104 is affixed to the case 102 and the inner housing 108 is slidable relative to the outer housing 104. The inner housing 108 or the outer housing 104 is repositionable, blocking all or some of the inner housing 108 aperture 120 to control directionality and dosage of radiation exposure 602 and, selectively the treatment drug 604 delivery, or the treatment gas 606 delivery to the treatment site 204. The treatment drug 604 or the treatment gas 606 is released when the inner housing 108 aperture 120, the outer housing 104 aperture 116, and the case 102 aperture 128 are aligned allowing egress of the treatment drug 604 or the treatment gas 606 from the inner housing 108 into the treatment site 204.

A controller 300 comprises a microcontroller 302, a memory 314, a radiation detector 324, a wireless communication interface 304, and an activation control 308, the activation control 308 is used to reposition either the inner housing 108 or the outer housing 104. The memory 314 is encoded with instructions that when executed by the microcontroller 302 effectuates the method which begins in block 1102.

In block 1102, by way of the wireless communication interface 304, the treatment cycle is received from a digital device 512. The treatment cycle comprising a desired radiation dosage amount, one or more of an open period for certain of the inner housing 108 aperture 120 over a time period controlling radiation, from the radiation source 602, directionality and exposure dosage and, selectively treatment drug delivery 604 or treatment gas 606 delivery to the treatment site. The method moves to block 1104.

In block 1104, in accordance with the treatment cycle, the method transitions between blocks 1106, 1108, 1110, 1112, and 1114.

In block 1106, at least a portion of one of the inner housing 108 aperture 120 is exposed and not blocked by the outer housing 104, by slidably repositioning the outer housing 104 or the inner housing 108 engendering radiation exposure, from the radiation source 602 and, selectively the treatment drug delivery 604 or other treatment gas 606 delivery to the treatment site 204. The method moves to block 1108.

In block 1108, a radiation level is read by way of the radiation detector 324 proximate the radiation release capsule 100 and the treatment site 204 to determine the amount of radiation 602 that the treatment site is being exposed to. The method moves to block 1110.

In block 1110, the radiation level is compared to the desired radiation dosage amount associated with the treatment cycle. The method moves to block 1112.

In block 1112, the radiation level to the treatment site 204 is adjusted by slidably repositioning the outer housing 104 or the inner housing 108 to increase or decrease the radiation 602 level based on the step of comparing to ensure that the treatment site is receiving the prescribed desired radiation dosage amount. The method returns to the step of reading until the open period is complete and then the method moves to block 1114.

In block 1114, the inner housing 108 first aperture 120 is blocked with the outer housing 108 preventing radiation exposure 602 of the treatment site. The method can return to block 1104 until the treatment cycle is complete and then the method is exited.

Figure 13:
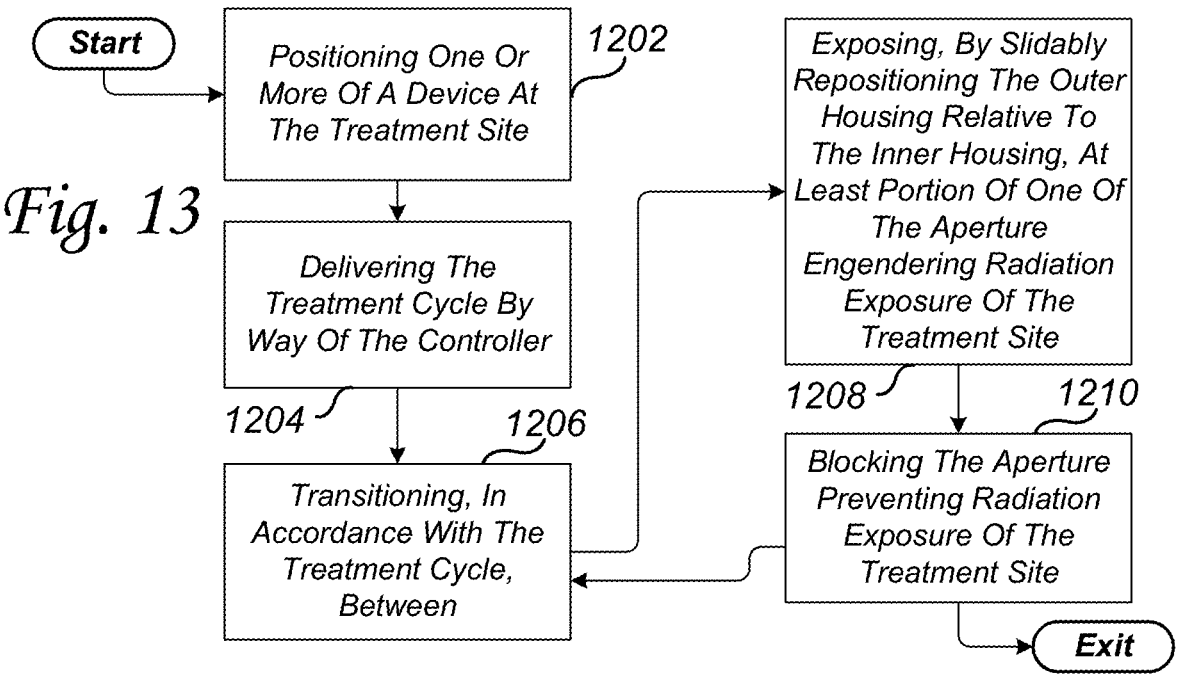

Referring to FIG. 13, there is illustrated one example of a method of controlling radiation exposure and selectively delivering treatment drugs or treatment gases at a treatment site associated with a treatment environment in accordance with a treatment cycle, the method begins in block 1202.

In block 1202, one or more of a radiation release capsule 100 is positioned to the treatment site 204, the radiation release capsule 100 comprises a controller 300, an inner housing 108, an outer housing 104, a case 102, and one or more of an activation control 308.

The inner housing 108 defines a cavity configured to at least encompass a radiation source 602 and, selectively a treatment drug 604 or a treatment gas 606. The inner housing is radiopaque and can comprise a radiation shielding disposed as a coating on the surface of the inner housing 108 or the inner housing 108 is manufactured from radiation shielding material.

The outer housing 104 comprises one or more of an aperture 116 disposed through the inner housing to selectively allow radiation from the radiation source 602 and, selectively the treatment drug 604 or the treatment gas 606 to be directionally released through one or more of the inner housing 108 aperture 120 during the treatment cycle. The outer housing 104 is radiopaque and can comprise a radiation shielding disposed as a coating on the surface of the outer housing 104 or the outer housing 104 is manufactured from radiation shielding material. The outer housing 104, selectively having one or more of an aperture 116 disposed through the outer housing. The outer housing 104 is positioned proximate to the inner housing 108.

The case 102 comprises, selectively a plurality of apertures 128 disposed through the case, the case is radiation permeable and surrounds the inner housing 108 and outer housing 104. Either the inner housing 108 is affixed to the case 102 and the outer housing 104 is slidable relative to the inner housing 108 or the outer housing 104 is affixed to the case 102 and the inner housing 108 is slidable relative to the outer housing 104. The inner housing 108 or the outer housing 104 is repositionable, blocking all or some of the inner housing 108 aperture 120 to control directionality and dosage of radiation exposure 602 and, selectively the treatment drug delivery 604, or the treatment gas 606 delivery to the treatment site 204.

The treatment drug 604 or the treatment gas 606 is released when the inner housing 108 aperture 120, the outer housing 104 aperture 116, and the case 102 aperture 128 are aligned allowing egress of the treatment drug 604 or the treatment gas 606 from the inner housing 108 into the treatment site 204. The method begins in block 1204.

In block 1204, the treatment cycle is delivered by way of a controller 300, the controller 300 comprises a microcontroller 302, a memory 314, and a housing position sensor 316. The memory 314 is encoded with instructions that when executed by the microcontroller 302 effectuate the method step in block 1206 of transitioning, in accordance with the treatment cycle, between blocks 1208 and 1210.

In this regard, in block 1208, at least a portion of one of the inner housing 108 aperture 120 is exposed and not blocked by the outer housing 104, by way of the activation control, by slidably repositioning the outer housing 104 or the inner housing 108 engendering radiation exposure, from the radiation source 602 and, selectively the treatment drug delivery 604 or other treatment gas 606 delivery to the treatment site 204. The method moves to block 1210.

In block 1210, the inner housing 108 aperture 120 is blocked, with the outer housing 116, preventing radiation exposure, from the radiation source 602 and, selectively the treatment drug release 604 or the treatment gas 606 release to the treatment site, by deactivating the activation control 308. The method can return to block 1206 until the treatment cycle is complete and then the method is exited.

Figure 14:
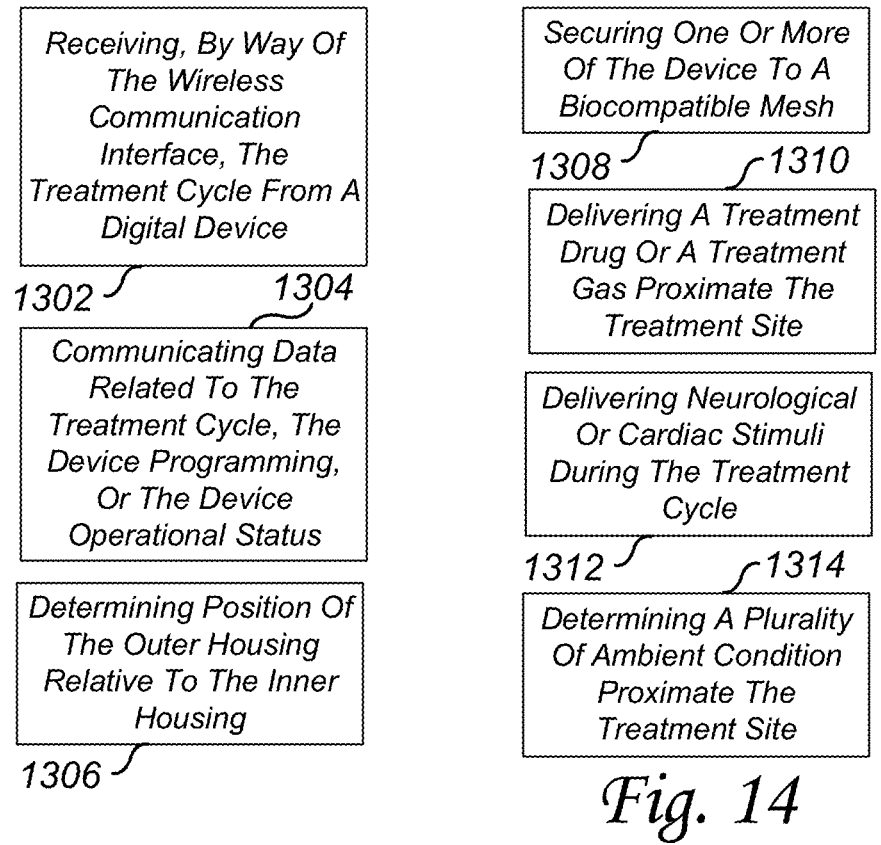
FIG. 14 illustrates exemplary embodiments of methods of controlling radiation exposure and selectively delivering treatment drugs or treatment gases at a treatment site associated with a treatment environment in accordance with a treatment cycle.

Referring to FIG. 14, there are illustrated exemplary embodiments of methods of controlling radiation exposure and selectively delivering treatment drugs or treatment gases at a treatment site associated with a treatment environment in accordance with a treatment cycle.

In block 1302, the treatment cycle is received, by way of a wireless communication interface 304, from a digital device 512, the treatment cycle comprising a plurality of opening and closing periods for certain of the inner housing 108 aperture 120 over a predetermined time period controlling radiation, from the radiation source 602, directionality and exposure dosage, treatment drug delivery 604, or treatment gas 606 delivery to the treatment site 204, the controller 300 comprises the wireless communication interface 304.

In block 1304, data or intelligent signals can be communicated related to the treatment cycle, the radiation release capsule 100 programming, or the radiation release capsule

100 operational status between the wireless communication interface 304 and co-located other of the radiation release capsule 100 or the digital device 512.

In block 1306, the position of the outer housing 104, relative to the inner housing 108 can be determined by way of a housing position sensor 316. The controller 300 comprises the housing position sensor 316.

In block 1308, one or more of the radiation release capsule 100 is secured to a biocompatible mesh 702, the biocompatible mesh 702 affixing the orientation of the radiation release capsule 100, relative to the biocompatible mesh 702, the biocompatible mesh 702 is secured proximate to the treatment site 204 preventing disorientation or migration of the radiation release capsule 100 during the treatment cycle.

In block 1310, a treatment drug 604 or a treatment gas 606 can be delivered proximate the treatment site 204.

In block 1312, neurological or cardiac stimuli can be delivered during the treatment cycle by way of an electromagnetic pulse generator 1318 that is operational related to the controller 300.

In block 1314, a plurality of ambient conditions can be determined proximate the treatment site, by way of an ambient condition sensor 320. In this regard, treatment site temperature, pressures, oxygen level, heart pulse, hydration, images of the treatment site from a camera incorporated into the ambient condition sensor 320, and other types and kinds of ambient conditions associated with the treatment site and proximate the radiation release capsule 100 can be determined and data communicated externally to digital devices 512, as may be required and/or desired in a particular embodiment.

The capabilities of the present invention can be implemented in software, firmware, hardware or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A radiation release capsule for controlling radiation exposure and selectively providing electromagnetic pulse therapy, electric field therapy, or treatment drug or gas delivery at a treatment site associated with a treatment environment in accordance with a treatment cycle, the radiation release capsule comprising:

an inner housing that is radiopaque, the inner housing defines a cavity configured to at least encompass a radiation source, the inner housing comprises one or more of an aperture disposed through the inner housing to allow radiation from the radiation source to be directionally released during the treatment cycle;

an outer housing is radiopaque and positioned proximate the inner housing; and a case is radiation permeable and surrounds the inner housing and outer housing, either the inner housing is stationary and the outer housing is slidable relative to the inner housing or the outer housing is stationary and the inner housing is slidable relative to the outer housing to control directionality and dosage of the radiation delivered to the treatment site by unblocking, blocking, or partially blocking the aperture.

2. The radiation release capsule in accordance with claim 1, further comprising:

a controller comprising a microcontroller, a memory, and an activation control, the memory, and the activation control are operationally related to the microcontroller.

3. The radiation release capsule in accordance with claim 2, the activation control is configured to slidably position either the inner housing or the outer housing by way of an electromagnet.

4. The radiation release capsule in accordance with claim 3, the memory is encoded with instructions that when executed by the microcontroller perform the following steps of:

receiving the treatment cycle from a digital device, by way of a wireless communication interface, the controller comprises the wireless communication interface, the wireless communication interface is operationally related to the microcontroller, in accordance with the treatment cycle the controller effectuates delivery of a desired radiation dosage amount for a prescribed treatment period by transitioning between:

exposing, by slidably positioning the outer housing or the inner housing so that at least portion of the aperture is unblocked by the outer housing engendering radiation delivery to the treatment site; and blocking the aperture, with the outer housing, preventing radiation delivery to the treatment site.

5. The radiation release capsule in accordance with claim 4, the memory is encoded with instructions that when executed by the microcontroller further comprise the step of:

communicating data or intelligent signals between the wireless communication interface and co-located other of the radiation release capsule or the digital device related to at least one of the following: the treatment cycle, the treatment site, the radiation release capsule, or operational status of the radiation release capsule.

6. The radiation release capsule in accordance with claim 4, the memory is encoded with instructions that when executed by the microcontroller further comprise the step of:

determining position of the outer housing relative to the inner housing by way of a housing position sensor, the controller comprising the housing position sensor, the housing position sensor is operationally related to the microcontroller.

7. The radiation release capsule in accordance with claim 2, the activation control is configured to slidably position either the inner housing or the outer housing by way of a shape-memory polymer, nitinol wire, a wire, or an elastomer.

8. The radiation release capsule in accordance with claim 1, further comprising:

a biocompatible mesh configured to receive one or more of the radiation release capsule, the biocompatible mesh affixing orientation of the radiation release capsule relative to the biocompatible mesh, the biocompatible mesh is securable proximate the treatment site and prevents disorientation or migration of the radiation release capsule during the treatment cycle.

9. The radiation release capsule in accordance with claim 8, the biocompatible mesh further comprising:
   a controller comprising a microcontroller, and a wireless communication interface, the wireless communication interface is operationally related to the microcontroller; and
   an antenna is operationally related to the wireless communication interface.

10. The radiation release capsule in accordance with claim 1, the cavity is further configured to hold one or more of the treatment drug or one or more of the treatment gas for controlled release proximate the treatment site during the treatment cycle.

11. The radiation release capsule in accordance with claim 1, further comprising:
   an electromagnetic pulse generator is configured to provide electromagnetic pulse therapy during the treatment cycle; and
   a controller comprising the electromagnetic pulse generator.

12. A radiation release capsule for controlling radiation exposure and selectively providing electromagnetic pulse therapy, electric field therapy, or treatment drug or gas delivery at a treatment site associated with a treatment environment in accordance with a treatment cycle, the radiation release capsule comprising:
   an inner housing that is radiopaque, the inner housing defines a cavity configured to at least encompass a radiation source, the inner housing comprises one or more of an aperture disposed through the inner housing to allow radiation from the radiation source to be directionally released during the treatment cycle;
   an outer housing is radiopaque and positioned proximate the inner housing;
   a case is radiation permeable and surrounds the inner housing and outer housing, either the inner housing is stationary and the outer housing is slidable relative to the inner housing or the outer housing is stationary and the inner housing is slidable relative to the outer housing to control directionality and dosage of radiation delivered to the treatment site by unblocking, blocking, or partially blocking the aperture;
   a controller comprising a microcontroller, a memory, a radiation detector, a wireless communication interface, and an activation control, is configured to slidably position either the inner housing or the outer housing, the memory, the radiation detector, the wireless communication interface, and the activation control are operationally related to the microcontroller, the memory is encoded with instructions that when executed by the microcontroller perform the steps of:
      receiving the treatment cycle from a digital device, by way of the wireless communication interface, in accordance with the treatment cycle the controller effectuates delivery of a desired radiation dosage amount for a prescribed treatment period to the treatment site by transitioning between:
         exposing, by slidably repositioning the outer housing or the inner housing so that at least portion of the aperture is unblocked by the outer housing engendering radiation delivery to the treatment site;
         reading direction of radiation and a radiation level by way of the radiation detector;
         comparing the radiation level to the desired radiation dosage amount;
         adjusting the radiation level to match the desired radiation dosage amount by slidably repositioning the outer housing or the inner housing to increase or decrease the radiation level accordingly, wherein returning to the step of reading until the prescribed treatment period is complete; and
         blocking the aperture, with the outer housing, preventing radiation delivery to the treatment site.

13. The radiation release capsule in accordance with claim 12, the memory is encoded with instructions that when executed by the microcontroller further comprise the step of:
   communicating data or intelligent signals between the wireless communication interface and co-located other of the radiation release capsule or the digital device related to at least one of the following: the treatment cycle, the treatment site, the radiation release capsule, or operational status of the radiation release capsule.

14. A method of controlling radiation exposure and selectively providing electromagnetic pulse therapy, electric field therapy, or treatment drug or gas delivery at a treatment site associated with a treatment environment in accordance with a treatment cycle, the method comprising the steps of:
   positioning one or more of a radiation release capsule at the treatment site, the radiation release capsule comprising a controller, an outer housing that is radiopaque, an inner housing that is radiopaque, the inner housing defines a cavity configured to at least encompass a radiation source, the inner housing comprises one or more of an aperture disposed through the inner housing to allow radiation from the radiation source to be directionally released during the treatment cycle, the outer housing is positioned proximate the inner housing, a case is radiation permeable and surrounds the inner housing and outer housing, either the inner housing is stationary and the outer housing is slidable relative to the inner housing or the outer housing is stationary and the inner housing is slidable relative to the outer housing to control directionality and dosage of radiation delivered to the treatment site by unblocking, blocking, or partially blocking the aperture;
   delivering radiation to the treatment site, by way of the controller in accordance with the treatment cycle, the controller comprising a microcontroller, a memory, and an activation control, the memory, and the activation control are operationally related to the microcontroller, the activation control is configured to slidably reposition either the inner housing or the outer housing, the memory is encoded with instructions that when executed by the microcontroller perform the steps of transitioning between:
      exposing, by slidably repositioning the outer housing or the inner housing so that at least portion of the aperture is unblocked by the outer housing engendering radiation delivery to the treatment site; and
      blocking the aperture, with the outer housing, preventing radiation delivery to the treatment site.

15. The method in accordance with claim 14, wherein at least one of the activation control operates an electromagnet or a shape-memory polymer.

16. The method in accordance with claim 14, further comprising the step of:

receiving the treatment cycle from a digital device, by way of a wireless communication interface, the controller comprises the wireless communication interface, the wireless communication interface is operationally related to the microcontroller.

17. The method in accordance with claim 14, further comprising the step of:
communicating data or intelligent signals between the wireless communication interface and co-located other of the radiation release capsule or a digital device related to at least one of the following: the treatment cycle comprising a desired radiation dosage amount for a prescribed treatment period, the treatment site, the radiation release capsule, or operational status of the radiation release capsule.

18. The method in accordance with claim 14, further comprising the step of:
determining a plurality of ambient conditions proximate the treatment site, by way of an ambient condition sensor, the controller comprises the ambient condition sensor, the ambient condition sensor is operationally related to the microcontroller.

19. The method in accordance with claim 14, further comprising the step of:
securing one or more of the radiation release capsule to a biocompatible mesh, the biocompatible mesh affixing the orientation of the radiation release capsule relative to the biocompatible mesh, the biocompatible mesh is secured proximate the treatment site preventing disorientation or migration of the radiation release capsule during the treatment cycle.

20. The method in accordance with claim 14, further comprising the step of:
delivering electromagnetic pulse therapy during the treatment cycle, by way of an electromagnetic pulse generator, the controller further comprising the electromagnetic pulse generator, the electromagnetic pulse generator is operationally related to the microcontroller.

\* \* \* \* \*